(12) United States Patent
Gao et al.

(10) Patent No.: US 12,350,381 B2
(45) Date of Patent: Jul. 8, 2025

(54) NANOPARTICLES CONTAINING CELLULAR MEMBRANE AND USES THEREOF

(71) Applicants: ARYTHA BIOSCIENCES, LLC, San Diego, CA (US); CELLICS THERAPEUTICS INC., San Diego, CA (US)

(72) Inventors: Weiwei Gao, San Diego, CA (US); Huiqing Zhu, San Diego, CA (US); Jian Guan, San Diego, CA (US); Yu-Wen Li, San Diego, CA (US)

(73) Assignees: ARYTHA BIOSCIENCES, LLC, San Diego, CA (US); CELLICS THERAPEUTICS INC., San Diego, CA (US)

( * ) Notice: Subject to any disclaimer, the term of this patent is extended or adjusted under 35 U.S.C. 154(b) by 136 days.

(21) Appl. No.: 17/296,200

(22) PCT Filed: Nov. 25, 2019

(86) PCT No.: PCT/US2019/063110
§ 371 (c)(1),
(2) Date: May 21, 2021

(87) PCT Pub. No.: WO2020/112694
PCT Pub. Date: Jun. 4, 2020

(65) Prior Publication Data
US 2022/0362162 A1 Nov. 17, 2022

Related U.S. Application Data

(60) Provisional application No. 62/771,561, filed on Nov. 26, 2018.

(51) Int. Cl.
*A61K 9/50* (2006.01)
*A61K 9/127* (2025.01)

(52) U.S. Cl.
CPC .......... *A61K 9/5068* (2013.01); *A61K 9/127* (2013.01); *A61K 9/5015* (2013.01); *A61K 9/5089* (2013.01)

(58) Field of Classification Search
None
See application file for complete search history.

(56) References Cited

U.S. PATENT DOCUMENTS

| | | | |
|---|---|---|---|
| 4,321,259 | A | 3/1982 | Nicolau et al. |
| 11,359,058 | B2 | 6/2022 | Gao et al. |
| 2008/0317767 | A1 | 12/2008 | Braxmeier et al. |
| 2013/0295159 | A1 | 11/2013 | Kester et al. |
| 2013/0337066 | A1 | 12/2013 | Zhang et al. |
| 2017/0360706 | A1 | 12/2017 | Ghoroghchian |

FOREIGN PATENT DOCUMENTS

| | | |
|---|---|---|
| CN | 103857387 A | 6/2014 |
| CN | 108699253 A | 10/2018 |
| CN | 114206360 A | 3/2022 |
| JP | 59157033 A | 9/1984 |
| JP | 2007238568 A | 9/2007 |
| JP | 5726620 A | 6/2015 |
| JP | 7518830 B2 | 7/2024 |
| JP | 2024133629 A | 10/2024 |
| WO | 2016090111 A1 | 6/2016 |
| WO | 2016144376 A1 | 9/2016 |
| WO | WO-2019022671 A1 * | 1/2019 .......... A61K 9/1075 |

OTHER PUBLICATIONS

Dodge, James T., Carolyn Mitchell, and Donald J. Hanahan. "The preparation and chemical characteristics of hemoglobin-free ghosts of human erythrocytes." Archives of biochemistry and biophysics 100.1 (1963): 119-130. (Year: 1963).*
Hoffman, Joseph F. "Biconcave shape of human red-blood-cell ghosts relies on density differences between the rim and dimple of the ghost's plasma membrane." Proceedings of the National Academy of Sciences 113.51 (2016): 14847-14851. (Year: 2016).*
Chakrabarti, Rima S., et al. "Variability of cholesterol accessibility in human red blood cells measured using a bacterial cholesterol-binding toxin." eLife 6 (2017): e23355. (Year: 2017).*
Zhang, Xinxin, et al. "Remote loading of small-molecule therapeutics into cholesterol-enriched cell-membrane-derived vesicles." Angewandte Chemie International Edition 56.45 (Oct. 5, 2017): 14075-14079 and S1-S5. (Year: 2017).*
Li, Cunbo, et al. "Protection of the biconcave profile of human erythrocytes against osmotic damage by ultraviolet-A irradiation through membrane-cytoskeleton enhancement." Cell Death Discovery 3.1 (2017): 1-10. (Year: 2017).*
Bogdanova A, Kaestner L, Simionato G, Wickrema A and Makhro A (2020) Heterogeneity of Red Blood Cells: Causes and Consequences. Front. Physiol. 11:392. doi: 10.3389/fphys.2020.00392 (Year: 2020).*
Written Opinion of the International Searching Authority for International Application No. PCT/US2019/063110, mailed Feb. 21, 2020 (11 pages).
PCT International Search Report for International Application No. PCT/US2019/063110, mailed Feb. 21, 2020 (3 pages).

(Continued)

*Primary Examiner* — Bethany P Barham
*Assistant Examiner* — Peter Anthopolos

(57) ABSTRACT

The present disclosure relates to nanoparticles containing cellular membrane and uses thereof. The nanoparticle comprises an interior compartment (or an inner core) and an outer surface (or shell) comprising a cellular membrane derived from a cell, said interior compartment (or an inner core) not providing a solid support to said cellular membrane in said outer surface (or shell). The present disclosure also relates to processes of making the nanoparticles. The present disclosure further relates to compositions comprising the nanoparticles and methods of using the nanoparticles.

16 Claims, 8 Drawing Sheets

(56) References Cited

OTHER PUBLICATIONS

PCT International Preliminary Report on Patentability for International Application No. PCT/US2019/063110, issued May 25, 2021 (12 pages).
Communication to Rule 161(2) and 162 EPC for European Patent Application 19 889 860.3, dated Jul. 9, 2021 (3 pages).
Response to Communication to Rule 161(2) and 162 EPC for European Patent Application 19 889 860.3, dated Jan. 18, 2022 (3 pages).
Marked-Up Claims for European Patent Application 19 889 860.3, dated Jan. 18, 2022 (34 pages).
Bonarska-Kujawa, et al. "Interaction of Selected Anthocyanins with Erythrocytes and Liposome Membranes". Cellular & Molecular Biology Letters, vol. 17: 289-308 (2012).
Enomoto, et al. "Asymmetric Binding of Cytochrome b5 to the Membrane of Human Erythrocyte Ghosts". Biochimica et Biophysica Acta, vol. 466: 136-147 (1977).
Shiga, et al. "Erythrocyte Rheology". Critical Reviews in Oncology/Hematology, vol. 10(1): 9-48 (1990).
Zhang, et al. "Remote Loading of Small-Molecule Therapeutics into Cholesterol-Enriched Cell-Membrane-Derived Vesicles". Angew. Chem. Int. Ed., vol. 56: 14075-14079 (2017).
Extended European Search Report from European Patent Application 19 889 860.3, dated Sep. 8, 2022 (10 pages).
Response to Communication Pursuant to Rules 70(2) and 70a(2) EPC from European Patent Application 19 889 860.3, dated Apr. 4, 2023 (14 pages).
Marked-Up Claims from European Patent Application 19 889 860.3, dated Apr. 4, 2023 (5 pages).
Communication Pursuant to Rules 70(2) and 70a(2) EPC from European Patent Application 19 889 860.3, dated Sep. 27, 2022 (1 page).
Amended Claims from Japanese Patent Application No. 2021-529714, filed Nov. 24, 2022 (24 pages).
Request for Examination from Japanese Patent Application No. 2021-529714, filed Nov. 24, 2022 (1 page).
Voluntary Amendment from Japanese Patent Application No. 2021-529714, filed Nov. 24, 2022 (23 pages).
Petition from Japanese Patent Application No. 2021-529714, filed Nov. 24, 2022 (2 pages).
English Version of the Amended Claims from Brazilian Application No. BR112021010125-0, dated Oct. 25, 2022 (4 pages).
Request for Examination and Voluntary Amendment as filed for Brazilian Application No. BR112021010125-0, dated Oct. 25, 2022 (116 pages).
Examination Request dated Oct. 19, 2023, AU App. No. 2019388869.
Postponement of Acceptance for Patent Application dated Oct. 19, 2023, AU App. No. 2019388869.
Office action dated Jul. 4, 2023, CN App. No. 201980089873.5.
Office action dated Aug. 31, 2023, JP App. No. 2021-529714.
Zhang, et al; "Remote Loading of Small-Molecule Therapeutics into Cholesterol-Enriched Cell-Membrane-Derived Vesicles"; Angew. Chem. Int. ED., 2017, vol. 56, pp. 14075-14079.
Acknowledgment Request for Examination dated Feb. 10, 2023, CA App. No. 3,120,860.
Response as Filed on Nov. 17, 2023 for the First Office Action, CN Application No. 201980089873.5.
Claims as Filed on Nov. 17, 2023, CN Application No. 201980089873.5.
Amended Claims as Filed on Dec. 5, 2023 for Japanese Patent Application No. 2021-529714.
Response as filed on Dec. 5, 2023, for Japanese Patent Application No. 2021-529714.
Amendment as filed on Dec. 5, 2023, for Japanese Patent Application No. 2021-529714.
CN Application No. 201980089873.5, Third office action dated Jul. 23, 2024.
Examiner's Report dated Jan. 16, 2024, Canadian Patent Application No. 3,120,860
Response to Exam Report dated May 15, 2024, Canadian Patent Application No. 3,120,860.
Second Office action dated Apr. 19, 2024, Chinese Application No. 201980089873.5.
Response to Second Office action dated Jun. 17, 2024, Chinese Application No. 201980089873.5.
Third Office action dated Jul. 23, 2024, Chinese Application No. 201980089873.5.
Official Action dated Feb. 14, 2024, Japanese Patent Application No. 2021-529714.
Amendment dated May 17, 2024, Japanese Patent Application No. 2021-529714.
Argument dated May 17, 2024, Japanese Patent Application No. 2021-529714.
Amended claims dated May 17, 2024, Japanese Patent Application No. 2021-529714.
Allowed claims dated Jun. 5, 2024, Japanese Patent Application No. 2021-529714.
Notice of Allowance dated Jun. 5, 2024, Japanese Patent Application No. 2021-529714.
CN Application No. 201980089873.5; English translation of the third Office Action.
CN Application No. 201980089873.5; Response to the third Office Action.
CN Application No. 201980089873.5; amended claims filed with the Response to the third Office Action.
CN Application No. 201980089873.5; Notification of Going Through the Formalities of Registration.
CN Application No. 201980089873.5; Notification of Granting Invention Patent Right issued by the CNIPA.

\* cited by examiner

NANOPARTICLES CONTAINING CELLULAR MEMBRANE AND USES THEREOF

I. RELATED APPLICATION

The present application is a U.S. national phase filing of International Patent Application Serial No. PCT/US2019/063110, filed on Nov. 25, 2019, entitled "NANOPARTICLES CONTAINING CELLULAR MEMBRANE AND USES THEREOF," which claims priority to U.S. provisional patent application No. 62/771,561, filed on Nov. 26, 2018. The contents and disclosures of the above applications are incorporated herein by reference in their entireties for all purposes.

II. FIELD OF THE INVENTION

The present disclosure relates to nanoparticles containing cellular membrane and uses thereof. The nanoparticle comprises an interior compartment (or an inner core) and an outer surface (or shell) comprising a cellular membrane derived from a cell, said interior compartment (or an inner core) not providing a solid support to said cellular membrane in said outer surface (or shell). The present disclosure also relates to processes of making the nanoparticles. The present disclosure further relates to compositions comprising the nanoparticles and methods of using the nanoparticles.

III. BACKGROUND OF THE INVENTION

WO 2013/052167 A2 relates to membrane encapsulated nanoparticles and method of use. Zhang et al., *Angew. Chem. Int. Ed.* 2017, 56:14075-14079 relates to remote loading of small-molecule therapeutics into cholesterol-enriched cell-membrane-derived vesicles. Ying et al., *Adv. Funct. Mater.* 2018, 28, 1801032 relates to remote-loaded platelet vesicles for disease-targeted delivery of therapeutics. Brian et al., *Nature Biotechnology*, 33:81-88 (2015) relates to engineered liposomes that sequester bacterial exotoxins and protect from severe invasive infections in mice.

Novel nanoparticles containing cellular membrane are needed. The present invention addresses this and the related needs in the art.

IV. SUMMARY OF THE INVENTION

In one aspect, the present disclosure provides for a nanoparticle comprising an interior compartment (or an inner core) and an outer surface (or shell) comprising a cellular membrane derived from a cell, said interior compartment (or an inner core) not providing a solid support to said cellular membrane in said outer surface (or shell), and wherein: a) said interior compartment (or inner core) is isotonic to a cellular or physiological liquid, e.g., an interior compartment (or an inner core) comprising a liquid that is isotonic to a cellular or physiological liquid; and/or b) said cellular membrane of said outer surface (or shell) comprises an enhanced or enriched level of a steroid, provided that when said cellular membrane is derived from a red blood cell, said interior compartment (or inner core) is isotonic to a cellular or physiological liquid.

In another aspect, the present disclosure provides a nanoparticle comprising an interior compartment (or an inner core) and an outer surface (or shell), wherein said interior compartment (or an inner core) does not provide a solid support to said outer surface (or shell) and/or is isotonic to a cellular or physiological liquid, e.g., an interior compartment (or an inner core) comprising a liquid that is isotonic to a cellular or physiological liquid, and said outer surface (or shell) comprises a cellular membrane derived a cell, cholesterol and sphingomyelin.

In still another aspect, the present disclosure provides a process for making a nanoparticle comprising: a) contacting a cellular membrane derived from a cell with a steroid to form a combination; and b) exerting exogenous energy on said combination in a liquid to form a nanoparticle comprising an interior compartment (or an inner core) and an outer surface (or shell) comprising said cellular membrane comprising an enhanced or enriched level of said steroid. In still another aspect, the present disclosure provides a process for making a nanoparticle comprising: a) contacting a cellular membrane derived from a cell with a steroid to form a combination; and b) exerting exogenous energy on said combination to form a nanoparticle comprising an interior compartment (or an inner core) and an outer surface comprising said cellular membrane comprising an enhanced or enriched level of said steroid; and c) exerting exogenous energy on said nanoparticle in a liquid that is isotonic to a cellular or physiological liquid to form a nanoparticle comprising said interior compartment (or an inner core) comprising said liquid that is isotonic to a cellular or physiological liquid and said outer surface comprising said cellular membrane comprising said enhanced or enriched level of said steroid. In still another aspect, the present disclosure provides a process for making a nanoparticle, comprising exerting exogenous energy on a cellular membrane derived from a red blood cell in a liquid that is isotonic to a cellular or physiological liquid to form a nanoparticle comprising an interior compartment (or an inner core) comprising said liquid that is isotonic to a cellular or physiological liquid and an outer surface comprising said cellular membrane.

In yet another aspect, the present disclosure provides for a process for making a nanoparticle, comprising: a) contacting a cellular membrane derived from a cell with a steroid and a sphingolipid dissolved in a water-miscible solvent to form a combination; and b) exerting exogenous energy on said combination, e.g., combination in a liquid, to form a nanoparticle comprising an interior compartment (or an inner core) and an outer surface (or shell) comprising said cellular membrane, said steroid and said sphingolipid.

Nanoparticles made by the above-described processes are also provided.

In yet another aspect, the present disclosure provides for a medicament delivery system or device, which comprises an effective amount of the above-described nanoparticle.

In yet another aspect, the present disclosure provides for a pharmaceutical composition comprising an effective amount of the above-described nanoparticle and a pharmaceutically acceptable carrier or excipient.

In yet another aspect, the present disclosure provides a method for treating or preventing a disease or condition in a subject in need comprising administering to said subject an effective amount of a nanoparticle comprising an interior compartment (or an inner core) and an outer surface (or shell) comprising a cellular membrane derived from a cell, said interior compartment (or an inner core) not providing a solid support to said cellular membrane in said outer surface (or shell). Optionally, and in some embodiments: a) said interior compartment (or inner core) of said nanoparticle is isotonic to a cellular or physiological liquid, e.g., an interior compartment (or an inner core) comprising a liquid that is isotonic to a cellular or physiological liquid; and/or b) said cellular membrane of said outer surface (or shell) of said nanoparticle comprises an enhanced or enriched level of a steroid. Further optionally, and in some embodiments; when the nanoparticle comprises a cellular membrane that is derived from a red blood cell, the interior compartment (or inner core) is isotonic to a cellular or physiological liquid. In some embodiments, the nanoparticle(s) is administered using a medicament delivery system or pharmaceutical composition comprising the nanoparticle(s).

In yet another aspect, the present disclosure provides a use of an effective amount of the above-described nanoparticle for the manufacture of a medicament for treating or preventing a disease or condition in a subject in need.

In yet another aspect, the present disclosure provides for an immunogenic composition, which comprises an effective amount of the above-described nanoparticle, and optionally further comprises an immunogenic adjuvant or an immunopotentiator. A vaccine comprising the above-described neoplasm specific immunogenic composition is also provided. A method for treating or preventing a neoplasm in a subject using the immunogenic composition or the vaccine is further provided. Use of an effective amount of the neoplasm specific immunogenic composition for the manufacture of a vaccine for treating or protecting a subject against a neoplasm is further provided.

In yet another aspect, the present disclosure provides for an immunogenic composition, which is configured for treating or preventing a disease or condition associated with a moiety that targets or binds to the cellular membrane of the nanoparticle; and wherein the outer surface of the nanoparticle comprises the moiety. A vaccine comprising the above-described immunogenic composition is also provided. A method for eliciting an immune response to a moiety associated with a disease or condition in a subject, using the immunogenic composition or the vaccine is further provided. Use of an effective amount of the immunogenic composition for the manufacture of a vaccine for protecting a subject against a disease or condition associated with the moiety is further provided.

In some embodiments, the present nanoparticles, medicament delivery systems, pharmaceutical compositions and methods, can be used to deliver the exemplary medications listed in the Orange Book: Approved Drug Products with Therapeutic Equivalence Evaluations (Current through March 2012) published by the U.S. Food and Drug Administration, the exemplary medications listed in *The Merck Index* (a U.S. publication, the printed 14th Edition, Whitehouse Station, N.J., USA) and its online version (The Merck Index Onlines$^{SM}$, Last Loaded on Web: Tuesday, May 1, 2012), and the exemplary medications listed in Biologics Products & Establishments published by the U.S. Food and Drug Administration, and can be used to treat or prevent the corresponding diseases and disorders.

In some aspects, the prevent disclosure relates to U.S. application Ser. No. 13/827,906, filed Mar. 14, 2013, and published as US 2013/337066 A1, International Application No. PCT/US2012/039411, filed May 24, 2012 and published as WO 2013/052167 A2 and U.S. provisional application Ser. No. 61/492,626, filed Jun. 2, 2011. The contents of the above applications are incorporated by reference in their entireties.

V. BRIEF DESCRIPTION OF THE DRAWINGS

Those of skill in the art will understand that the drawings, described below, are for illustrative purposes only. The drawings are not intended to limit the scope of the present teachings in any way.

FIG. 1 illustrates formulation and characterization of cholesterol-enriched RBC membrane vesicles (Cho-RBC-V). (A) The loading yield of exogenous cholesterol at different initial cholesterol loading. (B) Leakage of calcein from Cho-RBC-V (10% initial loading) compared with membrane vesicles without adding exogenous cholesterol. (C) Dose-dependent neutralization of MRSA culture supernatant against RBC hemolysis. In all studies, data represent mean±SD, n=3.

FIG. 2 illustrates formulation and characterization of cholesterol-enriched platelet membrane vesicles (Cho-PL-V). (A) The loading yield of exogenous cholesterol at different initial cholesterol loading. (B) Leakage of calcein from Cho-PL-V (10% initial loading) compared with membrane vesicles without adding exogenous cholesterol. (C) Dose-dependent neutralization of anti-platelet antibody with Cho-PL-V. In all studies, data represent mean±SD, n=3.

FIG. 3 illustrates formulation and characterization of cholesterol-enriched macrophage membrane vesicles (Cho-MΦ-V). (A) The loading yield of exogenous cholesterol at different initial cholesterol loading. (B) Leakage of calcein from Cho-MΦ-V (10% initial loading) compared with membrane vesicles without adding exogenous cholesterol. (C) Dose-dependent neutralization of LPS (endotoxin), as reflected by reduced IL-6 production in culture by macrophage cells. In all studies, data represent mean±SD, n=3.

FIG. 4 illustrates formulation and characterization of cholesterol-enriched neutrophhil membrane vesicles (Cho-Neu-V). (A) The loading yield of exogenous cholesterol at different initial cholesterol loading. (B) Leakage of calcein from Cho-Neu-V (10% initial loading) compared with membrane vesicles without adding exogenous cholesterol. (C) Dose-dependent neutralization of-TNF-α. In all studies, data represent mean±SD, n=3.

FIG. 5 illustrates an exemplary process for making Composition A comprising a nanoparticle comprising an interior compartment (or an inner core) and an outer surface (or shell), wherein said interior compartment (or inner core) does not provide a solid support to said outer surface (or shell), and said outer surface (or shell) comprises a plasma membrane derived a red blood cell, cholesterol and sphingomyelin.

FIG. 6 illustrates particle size distribution of an exemplary Composition A.

FIG. 7 illustrates exemplary in vivo efficacy of Composition A. A. Survival curves within the first 48 hours after bacterial challenge and formulation treatment. B. Bacterial loads in lung tissues harvested from mice survived for 48 hours after bacterial challenge and formulation treatment. Data were analyzed using the Log-rank (Mantal-Cox) test (A) and the Student-t test (B). CFU counts in the lungs harvested from the individual mice survived for 48 hours post challenge/treatment were log transformed, and plotted in FIG. 7B. The pulmonary bacterial count in mice treated with Composition A was significantly lower than that in the mice treated with the vehicle.

FIG. 8 illustrates exemplary reproducible effects of Composition A on survival rate. A. Survival curves from a single study in which 2 different lots of Composition A, 5-257-06 and 5-257-16, were intratracheally dosed in mice immediately after intratracheal instillation with MRSA. *p<0.05; **p<0.01. B. Survival curves averaged from 3 separate studies in which 3 lots of Composition A, 5-257-06, 5-257-16 and 5-260-02, were intratracheally dosed in mice immediately after intratracheal instillation with MRSA. Data are expressed as mean SEM. The survival rates in the vehiclevs. lot-treated groups at each time point (19, 26, 48 or 96 hours) were analyzed using the unpaired Student t-test. *p<0.05; **p<0.01.

FIG. 9 illustrates exemplary dose-curve effects of Composition A on survival rate. Lot 5-266-01 was used in the study. Survival date was pooled from 4 independent tests with a total of 40 mice dosed with vehicle, 5-266-01 at 19 mg/kg or 2 mg/kg, and a total of 30 mice dosed with 5-266-01 at 6 mg/kg.

FIG. 10 illustrates exemplary effects of Composition A on pulmonary bacterial loads. Composition A lot 5-257-16 was dosed at 22.5 mg/kg or the vehicle. The lungs of the mice were harvested 24 hours after challenge/treatment.

FIG. 11 illustrates exemplary characterization of DiR-Composition A in vitro. The top panel table shows dynamic light scattering data of DiR-Composition A. The bottom graph shows the stability of fluorescence intensity of DiR-Composition A after dialysis for up to 180 hours.

FIG. 12 illustrates exemplary pulmonary uptake and distribution of DiR-Composition A after intratracheal administration. Times indicate minutes or hours after intratracheal administration of DiR-Composition A. Each sample represent a single mouse lung.

VI. DETAILED DESCRIPTION OF THE INVENTION

Figure 1:
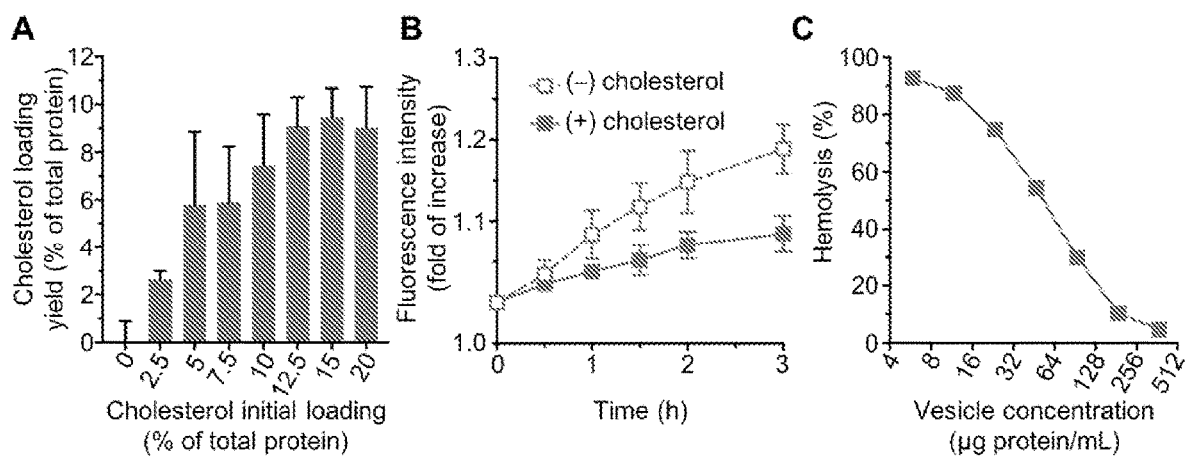
Figure 2:
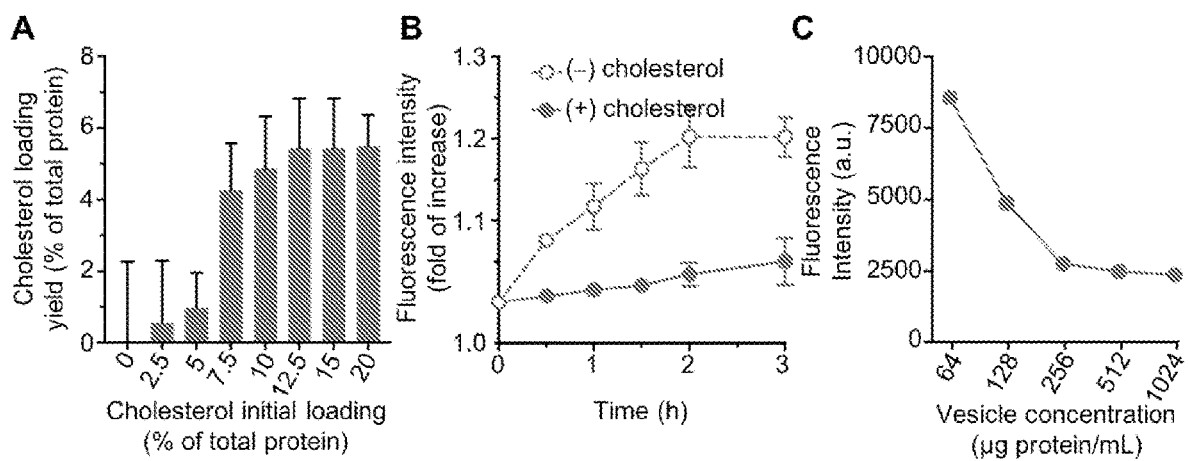
Figure 3:
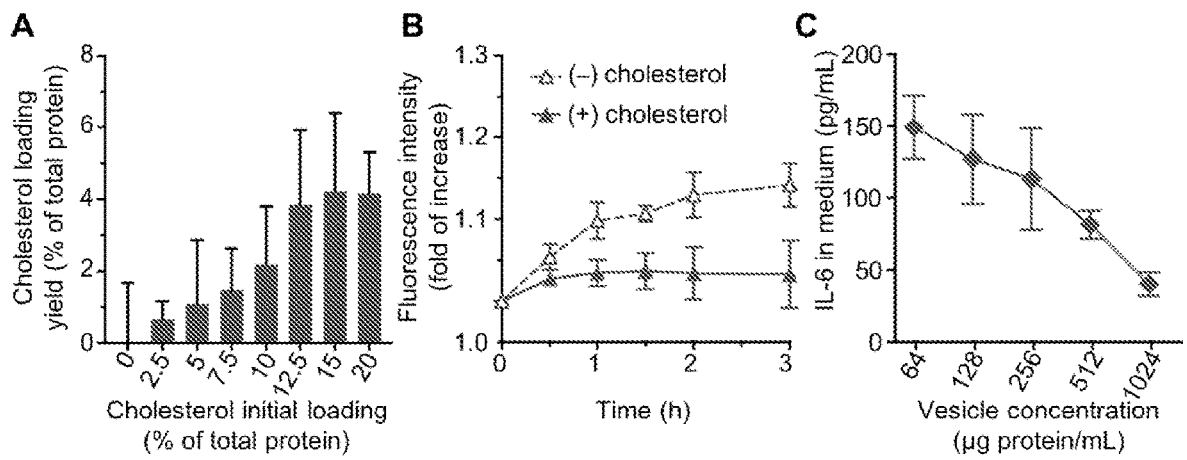
Figure 4:
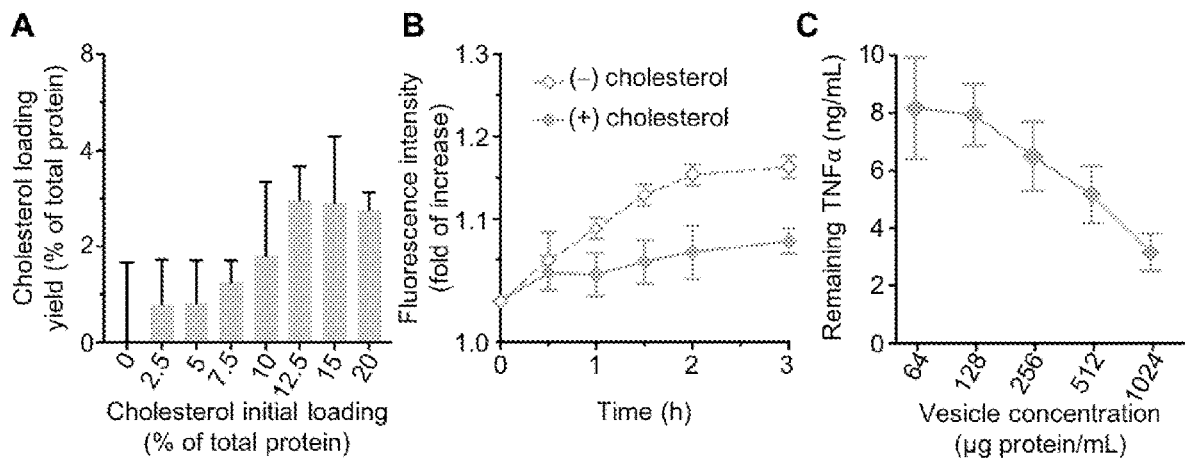
Figure 5:
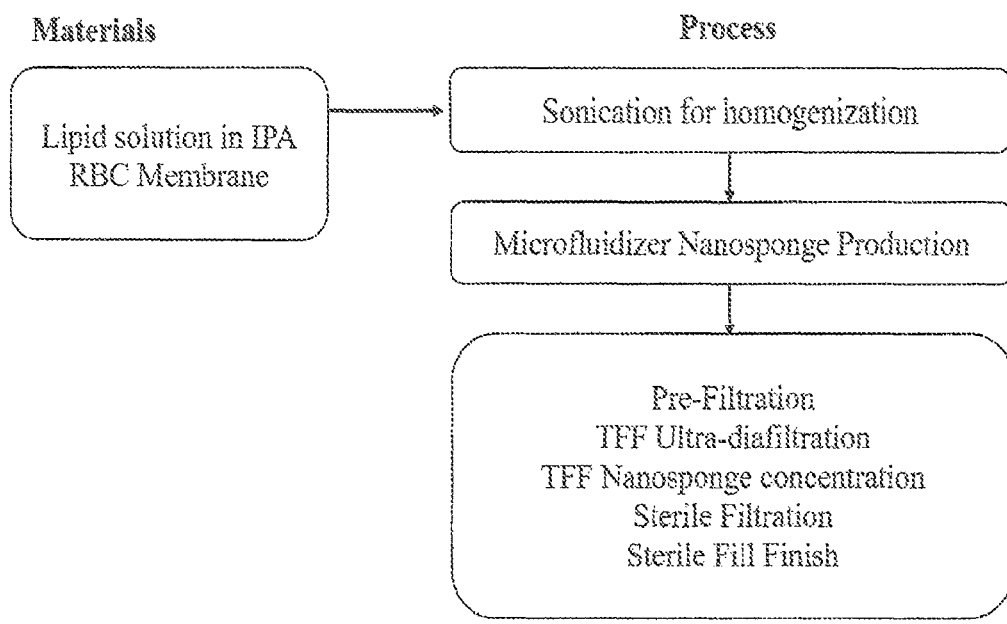

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, Molecular Cloning: A Laboratory Manual, 2nd ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, 20$^{th}$ ed., (Lippincott, Williams & Wilkins 2003), and Remington, The Science and Practice of Pharmacy, 22$^{th}$ ed., (Pharmaceutical Press and Philadelphia College of Pharmacy at University of the Sciences 2012).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Cellular Membrane: The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term "naturally occurring" refers to one existing in nature. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce "non-natural" substances that are incorporated into its membrane in vivo, and the cellular or viral membrane can be prepared or isolated from the cell or the virus to form a derived membrane.

In various embodiments, the cellular membrane covering either of the unilamellar or multilamellar nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibodies and aptamers can be added to the outer surface of the membrane to enhance site targeting, such as to cell surface epitopes found in cancer cells. The membrane of the nanoparticles can also comprise particles that can be biodegradable, cationic nanoparticles including, but not limited to, gold, silver, and synthetic nanoparticles.

Synthetic or artificial membrane: As used herein, the term "synthetic membrane" or "artificial membrane" refers to a man-made membrane that is produced from organic material, such as polymers and liquids, as well as inorganic materials. A wide variety of synthetic membranes are well known in the art.

Nanoparticle: In some embodiments, the term "nanoparticle" as used herein refers to nanostructure, particles, vesicles, or fragments thereof having at least one dimension (e.g., height, length, width, or diameter) of between about 1 nm and about 10 µm. For systemic use, an average diameter of about 30 nm to about 500 nm, or about 30 nm to about 300 nm, or about 50 nm to about 250 nm may be preferred. The term "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. In some embodiments, the nanoparticle comprising or consisting of an interior compartment (or an inner core) covered by an outer surface (or shell) comprising the membrane as discussed herein. The disclosure contemplates any nanoparticles now known and later developed that can be coated with the membrane described herein.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of the compounds, such as the multi-drug conjugates, in the present disclosure. A pharmaceutically acceptable salt is any salt which retains the activity of the parent nanoparticle or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66: 1, 1977). In some embodiments, a "pharmaceutically acceptable salt" is intended to mean a salt of a free acid or base of a nanoparticle or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A nanoparticle or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

Pharmaceutically acceptable carrier: The term "pharmaceutically acceptable carrier" as used herein refers to an excipient, diluent, preservative, solubilizer, emulsifier, adjuvant, and/or vehicle with which a nanoparticle or compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20'" ed., (Lippincott, Williams & Wilkins 2003). Except insofar as any conventional media or agent is incompatible with the active compound, such use in the compositions is contemplated.

Phospholipid: The term "phospholipid", as used herein, refers to any of numerous lipids contain a diglyceride, a phosphate group, and a simple organic molecule such as choline. Examples of phospholipids include, but are not limited to, Phosphatide acid (phosphatidate) (PA), Phosphatidylethanolamine (cephalin) (PE), Phosphatidylcholine (lecithin) (PC), Phosphatidylserine (PS), and Phosphoinositides which include, but are not limited to, Phosphatidylinositol (PI), Phosphatidylinositol phosphate (PIP), Phosphatidylinositol bisphosphate (PIP2) and Phosphatidylinositol triphosphate (P1P3). Additional examples of PC include DDPC, DLPC, DMPC, DPPC, DSPC, DOPC, POPC, DRPC, and DEPC as defined in the art.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as a hemolytic disease or condition, or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

The term "combination" refers to either a fixed combination in one dosage unit form, or a kit of parts for the combined administration where a nanoparticle or compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a nanoparticle or compound and a combination partner, are both administered to a patient simultaneously in the form of a single entity or dosage. The term "non-fixed combination" means that the active ingredients, e.g., a nanoparticle or compound and a combination partner, are both administered to a patient as separate entities either simultaneously, concurrently or sequentially with no specific time limits, wherein such administration provides therapeutically effective levels of the two moieties or compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

B. Nanoparticles Containing Cellular Membrane

In one aspect, the present disclosure provides for a nanoparticle a nanoparticle comprising an interior compartment (or an inner core) and an outer surface (or shell) comprising a cellular membrane derived from a cell, said interior compartment (or an inner core) not providing a solid support to said cellular membrane in said outer surface (or shell), and wherein: a) said interior compartment (or inner core) is isotonic to a cellular or physiological liquid, e.g., an interior compartment (or an inner core) comprising a liquid that is isotonic to a cellular or physiological liquid; and/or b) said cellular membrane of said outer surface (or shell) comprises an enhanced or enriched level of a steroid, provided that when said cellular membrane is derived from a red blood cell, said interior compartment (or inner core) is isotonic to a cellular or physiological liquid.

The interior compartment (or an inner core) of the present nanoparticle can be isotonic to a cellular or physiological liquid in any suitable manner. For example, the interior compartment (inner core) can comprise a liquid that is isotonic to a cellular or physiological liquid. In another example, the interior compartment (inner core) can comprise dry substance(s) that, when reconstituted with a liquid, forms a liquid that is isotonic to a cellular or physiological liquid.

The interior compartment (or an inner core) of the present nanoparticle can be isotonic to a cellular or physiological liquid in any suitable environment. For example, the interior compartment (inner core) can be isotonic to a cellular or physiological liquid existing outside a cell or a subject. In another example, the interior compartment (inner core) can be isotonic to a cellular or physiological liquid existing in a cell or a subject.

In some embodiments, the interior compartment (inner core) of the present nanoparticle can comprise a liquid that is isotonic to a cellular liquid comprised in a cell. In some embodiments, the interior compartment (inner core) of the present nanoparticle can comprise dry substance(s) that, when reconstituted with a liquid, forms a liquid isotonic to a cellular liquid existing in a cell.

The interior compartment (inner core) of the present nanoparticle can be isotonic to a cellular liquid comprised in any suitable cell. The cell can be a prokaryotic cell or a eukaryotic cell. In some embodiments, the cell can be a cell of a unicellular organism, e.g., a bacterium or a fungus. The cell can also be a cell of a multicellular organism, e.g., a plant, an animal, a vertebrate, a non-human mammal or a human.

In some embodiments, the cell is an animal cell, e.g., a non-human mammalian cell or a human cell. The cell can be any suitable animal cell. For example, the cell can be a cell of a connective tissue, e.g., blood, bone, tendon, ligament, adipose or areolar tissue, fibrous connective tissue, skeletal connective tissue, or fluid connective tissue. In another example, the cell can be a cell of a muscular tissue, e.g., visceral or smooth muscle, skeletal muscle or cardiac muscle. In still another example, the cell can be a cell of a nervous tissue, e.g., a cell in a central nervous system (CNS) or a peripheral nervous system (PNS). In yet another example, the cell can be a cell of an epithelial tissue, e.g., simple squamous epithelium, stratified squamous epithelium, simple cuboidal epithelium, transitional epithelium, pseudostratified columnar epithelium (also known as Ciliated columnar epithelium), columnar epithelium, glandular epithelium or ciliated columnar epithelium. In yet another example, the cell can be a cell of nervous system, cardiovascular system, circulatory system, vascular system, digestive system, endocrine system, immune system, integumentary system, lymphatic system, musculoskeletal system, reproductive system, respiratory system, respiratory apparatus, ventilatory system, urinary system, or renal system or urinary tract. In yet another example, the cell can be a blood cell, a tumor cell, a cancer cell, an immune cell, a stem cell, an endothelial cell, or an epithelial cell.

The interior compartment (inner core) of the present nanoparticle can be isotonic to a physiological liquid in any suitable environment. For example, the interior compartment (inner core) can be isotonic to a physiological liquid existing outside a cell or a subject. In another example, the interior compartment (inner core) can be isotonic to a physiological liquid existing in a cell or a subject.

The interior compartment (inner core) of the present nanoparticle can be isotonic to a physiological liquid in any suitable subject. For example, the interior compartment (inner core) can be isotonic to a physiological liquid in a multicellular organism, e.g., a plant, an animal, a vertebrate, a non-human mammal or a human. In some embodiments, the interior compartment (inner core) can be isotonic to a physiological liquid in an animal, a vertebrate, a non-human mammal or a human, e.g., circulating blood in an animal, a vertebrate, a non-human mammal or a human.

The interior compartment (inner core) of the present nanoparticle can be isotonic to any suitable physiological liquid. For example, the physiological liquid can be a physiological liquid of nervous system, cardiovascular system, circulatory system, vascular system, digestive system, endocrine system, immune system, integumentary system, lymphatic system, musculoskeletal system, reproductive system, respiratory system, respiratory apparatus, ventilatory system, urinary system, or renal system or urinary tract.

In some embodiments, the interior compartment (inner core) of the present nanoparticle comprises a liquid that is isotonic to a cellular or physiological liquid ex vivo. In other embodiments, the interior compartment (inner core) of the present nanoparticle comprises a liquid that is isotonic to a cellular or physiological liquid in vivo.

The interior compartment (inner core) of the present nanoparticle can comprise any suitable material. In some embodiments, the interior compartment (inner core) of the present nanoparticle does not support the outer surface (or shell). Any suitable material can be used. For example, the interior compartment (inner core) can comprise liquid only, e.g., a liquid that is isotonic to a cellular or physiological liquid, and such liquid does not support the outer surface (or shell), In another example, the interior compartment (inner core) does not comprise any solid material. In another example, the interior compartment (inner core) can comprise a solid material(s), e.g., dry substance(s) that, when reconstituted with a liquid, forms a liquid that is isotonic to a cellular or physiological liquid. Such material(s), however, is not sufficiently large and/or strong to support the outer surface (or shell).

The present nanoparticle can comprise any suitable cellular membrane derived from a cell or a cellular source, e.g., a red blood cell. For example, the nanoparticle can comprise a plasma membrane or an intracellular membrane derived from a cell, e.g., a red blood cell. In some embodiments, the cellular membrane comprises a plasma membrane derived from a red blood cell, e.g., a plasma membrane derived from a human red blood cell. In some embodiments, the nanoparticle can comprise any suitable naturally occurring cellular membrane derived from a cell, e.g., a red blood cell. In some embodiments, the cellular membrane comprises a naturally occurring plasma membrane derived from a red blood cell, e.g., a naturally occurring plasma membrane derived from a human red blood cell.

In some embodiments, the cellular membrane can be derived from a unicellular organism (e.g. a bacterium or fungus) or a multicellular organism (e.g., a plant, an animal, a non-human mammal, vertebrate, or a human). In other embodiments, the cellular membrane can be derived from a blood cell, e.g. a red blood cell, a white blood cell or a platelet. In still other embodiments, the cellular membrane can be derived from an immune cell (e.g., macrophage, monocyte, B-cell, or T-cell), a tumor or cancer cell, and other cells, such as an epithelial cell, an endothelial cell, or a neural cell. In yet other embodiments, the cellular membrane can be derived from a non-terminally differentiated cell, such as a stem cell, including a hematopoietic stem cell, a bone marrow stem cell, a mesenchymal stem cell, a cardiac stem cell, a neural stem cell. In yet other embodiments, the cellular membrane can be derived from a cell component or cell organelle including, but not limited to, an exosome, a secretory vesicle, a synaptic vesicle, an endoplasmic reticulum (ER), a Golgi apparatus, a mitochondrion, a vacuole or a nucleus.

In some embodiments, the cellular membrane is derived from a cell of an animal, a vertebrate, a non-human mammal or a human. The cellular membrane can be derived from any suitable type of cell. For example, the cellular membrane is derived from a cell of a connective tissue, e.g., blood, bone, tendon, ligament, adipose or areolar tissue, fibrous connective tissue, skeletal connective tissue, or fluid connective tissue. In another example, the cell is a cell of a muscular tissue, e.g., visceral or smooth muscle, skeletal muscle or cardiac muscle. In still another example, the cell is a cell of a nervous tissue, e.g., a cell in a central nervous system (CNS) or a peripheral nervous system (PNS). In yet another example, the cell is a cell of an epithelial tissue, e.g., simple squamous epithelium, stratified squamous epithelium, simple cuboidal epithelium, transitional epithelium, pseudostratified columnar epithelium (also known as Ciliated columnar epithelium), columnar epithelium, glandular epithelium or ciliated columnar epithelium. In yet another example, the cell is a cell of nervous system, cardiovascular system, circulatory system, vascular system, digestive system, endocrine system, immune system, integumentary system, lymphatic system, musculoskeletal system, reproductive system, respiratory system, respiratory apparatus, ventilatory system, urinary system, or renal system or urinary tract. In yet another example, the cell is a blood cell, a tumor cell, a cancer cell, an immune cell, a stem cell, an endothelial cell, or an epithelial cell. In yet another example, the cellular membrane comprises a plasma membrane derived from a blood cell, e.g., a red blood cell, a white blood cell and/or a platelet.

The outer surface (or shell) of the present nanoparticle can comprise an enhanced or enriched level of any suitable steroid. For example, the steroid can be a fungal steroid, an animal steroid, a plant steroid, or a prokaryotic steroid. Exemplary fungal steroids include ergosterol, ergosta-5,7, 22,24(28)-tetraen-3β-ol, Zymosterol, lanosterol, or 5,6-dihydroergosterol. The animal steroid can be a vertebrate steroid or an insect steroid. Exemplary insect steroid can be an ecdysteroid, e.g., 20-hydroxyecdysone (ecdysterone or 20E).

Exemplary vertebrate steroid can be a steroid hormone or cholesterol. In some embodiments, the vertebrate steroid can be cholesterol. In other embodiments, the steroid hormone can be a sex steroid, e.g., an androgen, an estrogen, or a progestogen, a corticosteroid, e.g., a glucocorticoid or a mineralocorticoid, or an anabolic steroid, e.g., testosterone or an ester thereof.

Exemplary plant steroid can be an alkaloid, a cardiac glycoside, a phytosterol, or a brassinosteroid. Exemplary prokaryotic steroid can be a tetracyclic steroid, or a triterpenes e.g., hopane.

In some embodiments, the steroid is a cholestane, e.g., cholesterol, a cholane, e.g., cholic acid, a pregnane, e.g., progesterone, an androstane, e.g., testosterone, or an estrane, e.g., estradiol. In other embodiments, the steroid is selected from the group consisting of a gonane, testosterone, cholic acid, dexamethasone, lanosterol, progesterone, medrogestone, β-sitosterol, cholesterol, and 5α-cholestane.

In some embodiments, the outer surface (or shell) comprises a cellular membrane derived from a fungal cell and the cellular membrane comprises an enhanced or enriched level of a fungal steroid. In other embodiments, the outer surface (or shell) comprises a cellular membrane derived from a plant cell and the cellular membrane comprises an enhanced or enriched level of a plant steroid. In still other embodiments, the outer surface (or shell) comprises a cellular membrane derived from a prokaryotic cell and the cellular membrane comprises an enhanced or enriched level of a prokaryotic steroid. In yet other embodiments, the outer surface (or shell) comprises a cellular membrane derived from an animal cell and the cellular membrane comprises an enhanced or enriched level of an animal steroid. In yet other embodiments, the outer surface (or shell) comprises a cellular membrane derived from a vertebrate cell and the cellular membrane comprises an enhanced or enriched level of a vertebrate steroid. In yet other embodiments, the outer surface (or shell) comprises a cellular membrane derived from a mammalian cell, e.g., a human cell, and the cellular membrane comprises an enhanced or enriched level of a mammalian steroid, e.g., a human steroid.

In some embodiments, the outer surface (or shell) comprises a cellular membrane derived from a blood cell and the cellular membrane comprises an enhanced or enriched level of a mammalian steroid, cholesterol. The outer surface (or shell) can comprise a cellular membrane derived from any suitable blood cell, e.g., a red blood cell, a white blood cell, or a platelet, and the cellular membrane comprises an enhanced or enriched level of a mammalian steroid, e.g., cholesterol. In some embodiments, the outer surface (or shell) comprises a plasma membrane derived from blood cell, e.g., a red blood cell, a white blood cell, and/or a platelet, and the cellular membrane comprises an enhanced or enriched level of a mammalian steroid, e.g., cholesterol. In some embodiments, the outer surface (or shell) comprises a plasma membrane derived from a human blood cell, e.g., a human red blood cell, a human white blood cell, and/or a human platelet, and the cellular membrane comprises an enhanced or enriched level of a human steroid, e.g., cholesterol.

The outer surface (or shell) of the present nanoparticle can comprise a steroid whose level is enhanced or enriched by any suitable manner. For example, the enhanced or enriched level of a steroid in the cellular membrane of the outer surface (or shell) can be due to the exogenously added steroid. In another example, the enhanced or enriched level of a steroid in the cellular membrane of the outer surface (or shell) can be due to the use of a cellular membrane derived from a cell that is modified to contain an enhanced or enriched level of the steroid in its membrane.

The cellular membrane of the outer surface (or shell) of the present nanoparticle can comprise any suitable level of a steroid. For example, the cellular membrane of the outer surface (or shell) can comprise a level of a steroid that is at least 0.1%, e g at least about 1%, 2%, 3%, 4%, 5%, 6%, 7%, 8%, 9%, 10%, 20%, 30%, 40%, 50%, 60%, 70%, 80%, 90%, 1 fold, 2 fold, 4 fold, 5 fold, or higher than the basal level of the steroid in the cellular membrane.

In some embodiments, the cellular membrane of the outer surface (or shell) can comprise from about 0.1% (w/w) to about 50% (w/w), e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%4, 40%, 41%, 42%, 43%, 44%, 45%, 46%, 47%, 48%, 49%, 50% of the exogenously added steroid. Optionally, the cellular membrane of the outer surface (or shell) can comprise from about 0.1% (w/w) to about 50% (w/w), e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% of the exogenously added steroid, as compared with total membrane protein weight of the cellular membrane. In some embodiments, the cellular membrane of the outer surface (or shell) can comprise a cellular membrane derived from a blood cell and comprises from about 0.1% (w/w) to about 50% (w/w), e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% of the exogenously added steroid, e.g., cholesterol. Optionally, the cellular membrane of the outer surface (or shell) can comprise a cellular membrane derived from a blood cell and comprises from about 0.1% (w/w) to about 50% (w/w), e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% of the exogenously added steroid, e.g., cholesterol, as compared with total membrane protein weight of the cellular membrane.

In some embodiments, the cellular membrane of the outer surface (or shell) can comprise from about 20% (w/w) to about 100% (w/w), e.g., about 20%, 30%, 40%, 50%, 60%, 70%, 80%, 90%, 95%, 96%, 97%, 98%, 99%, 99.9%, 99.99%, 99.999% or 100%, of the steroid. Optionally, the cellular membrane of the outer surface (or shell) can comprise from about 20% (w/w) to about 100% (w/w), e.g., about 20%, 30%, 40%, 50%, 60%, 70%, 80%, 90%, 95%, 96%, 97%, 98%, 99%, 99.9%, 99.99%, 99.999% or 100%, of the steroid, as compared with total membrane protein weight of the cellular membrane. In some embodiments, "100/" means equal amount or level of the steroid, e.g., cholesterol, and total membrane protein weight. In some embodiments, the cellular membrane of the outer surface (or shell) can comprise a cellular membrane derived from a blood cell and comprises from about 20% (w/w) to about 100% (w/w), e.g., about 20%, 30%, 40%, 50%, 60%, 70%, 80%, 90%, 95%, 96%, 97%, 98%, 99%, 99.9%, 99.99%, 99.999% or 100%, of the steroid, e.g., cholesterol. Optionally, the cellular membrane of the outer surface (or shell) can comprise a cellular membrane derived from a blood cell and comprises from about 20% (w/w) to about 100% (w/w), e.g., about 20%, 30%, 40%, 50%, 60%, 70%, 80%, 90%, 95%, 96%, 97%, 98%, 99%, 99.9%, 99.99%, 99.999% or 100%, of the steroid, e.g., cholesterol, as compared with total membrane protein weight of the cellular membrane.

The interior compartment (inner core) of the present nanoparticle can have any suitable pH. For example, the interior compartment (inner core) can have a pH ranging from about 4 to about 10, e.g., from about 6 to about 9, or at about 6, 6.5, 7, 7.5, 8, 8.5 or 9.

The present nanoparticle can further comprise a releasable cargo. The nanoparticle can comprise a releasable cargo at any suitable location. For example, the releasable cargo can be located within or on the interior compartment (inner core), between the interior compartment (inner core) and the outer surface (or shell), or within or on the outer surface (or shell). The release of the releasable cargo can be triggered by any suitable mechanisms. For example, the release of the releasable cargo can be triggered by a contact between the nanoparticle and the subject or by a change of a physical parameter surrounding the nanoparticle. The nanoparticle can comprise any suitable types of releasable cargo. For example, the releasable cargo can be a therapeutic agent, a prophylactic agent, a diagnostic or marker agent, a prognostic agent, or a combination thereof. The therapeutic agent can be a cytotoxic drug capable of cell killing. Any suitable cytotoxic drugs can be used. For example, cytotoxic drugs can be an anthracycline, e.g., doxorubicin or daunorubicin, a taxane, e.g., docetaxel or paclitaxel, or an immunosuppressive agent, e.g., methotrexate or cyclosporin A. In another example, the releasable cargo can be a metallic particle, a polymeric particle, a dendrimer particle, or an inorganic particle or the releasable cargo can be in the form of a metallic particle, a polymeric particle, a dendrimer particle, or an inorganic particle.

In some embodiments, the present nanoparticle does not comprise a releasable cargo.

The nanoparticle can have any suitable size. For example, the nanoparticle can have a diameter from about 10 nm to about 10 μm. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm, or any sub-range within about 10 nm to about 10 μm, e.g., any range between any two of the above sizes.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle substantially lacks constituents of the cell from which the cellular membrane is derived. For example, the nanoparticle can lack about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the cell e.g., red blood cell, from which the cellular membrane is derived. In some embodiments, the nanoparticle comprises a plasma membrane derived from a red blood cell and the nanoparticle substantially lacks hemoglobin. For example, the nanoparticle can lack about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle substantially maintains natural structural integrity or activity of the cellular membrane or the constituents of the cellular membrane. For example, the nanoparticle can retain about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity. In some embodiments, the nanoparticle substantially maintains natural structural integrity of the cellular membrane or the constituents of the cellular membrane including primary, secondary, tertiary and/or quaternary structure of the cellular membrane, or the constituents of the cellular membrane. In some embodiments, the nanoparticle substantially maintains activity of the cellular membrane or the constituents of the cellular membrane including binding activity, receptor activity and/or enzymatic activity of the cellular membrane, or the constituents of the cellular membrane.

The interior compartment (or an inner core) of the present nanoparticle can comprise any suitable substance. For example, the interior compartment (or an inner core) of the present nanoparticle can comprise any suitable substance to make the interior compartment (or an inner core) isotonic to a cellular or physiological liquid.

In some embodiments, the interior compartment (or an inner core) can comprise a salt, a sugar or a sugar alcohol. The interior compartment (or an inner core) can comprise any suitable salt, sugar or a sugar alcohol. For example, the sugar can be a monosaccharide or a disaccharide. Exemplary monosaccharide can be fructose, galactose or glucose. Exemplary disaccharide can be lactose, maltose or sucrose. Exemplary salt can be a sodium, potassium or magnesium salt, e.g., NaCl, KCl or $MgCl_2$.

In another example, the sugar alcohol can be ethylene glycol, glycerol, erythritol, threitol, arabitol (or arabinitol), xylitol, ribitol, (or adonitol), mannitol, sorbitol, galactitol (dulcitol), fucitol, iditol, inositol, volemitol, isomalt, maltitol, lactitol, maltotriitol, maltotetraitol or polyglycitol. In some embodiments, the sugar alcohol is sorbitol.

The sugar or the sugar alcohol can have any suitable osmolality or concentration. For example, the sugar or the sugar alcohol can have a osmolality from about 250 mmol/kg to about 350 mmol/kg, e.g., from about 275 mmol/kg to about 295 or 300 mmol/kg, or at about 250 mmol/kg, 260 mmol/kg, 270 mmol/kg, 280 mmol/kg, 290 mmol/kg, 295 mmol/kg or 300 mmol/kg. In another example, the sugar or the sugar alcohol can have a concentration ranging from about 250 mmol/kg to about 1,000 mmol/kg, e.g., at about 250 mmol/kg, 300 mmol/kg, 400 mmol/kg, 500 mmol/kg, 600 mmol/kg, 700 mmol/kg, 800 mmol/kg, 900 mmol/kg, or 1,000 mmol/kg.

In some embodiments, the interior compartment (or an inner core) can comprise a salt. The interior compartment (or an inner core) can comprise any suitable salt. For example, the salt can be a sodium, potassium or magnesium salt, e.g., NaCl, KCl or $MgCl_2$. The salt can have any suitable osmolality or concentration. For example, the salt can have a osmolality from about 250 mmol/kg to about 350 mmol/kg, e.g., from about 275 mmol/kg to about 295 or 300 mmol/kg, or at about 250 mmol/kg, 260 mmol/kg, 270 mmol/kg, 280 mmol/kg, 290 mmol/kg, 295 mmol/kg or 300 mmol/kg. In another example, the salt can have a concentration ranging from about 250 mmol/kg to about 1,000 mmol/kg, e.g., at about 250 mmol/kg, 300 mmol/kg, 400 mmol/kg, 500 mmol/kg, 600 mmol/kg, 700 mmol/kg, 800 mmol/kg, 900 mmol/kg, or 1,000 mmol/kg.

In some embodiments, the nanoparticle is biocompatible or biodegradable. For example, the inner core of the nanoparticle can comprise a biocompatible or biodegradable material and the outer surface of the nanoparticle comprises a plasma membrane derived from a cell, e.g., a red blood cell. In another example, the interior compartment (or an inner core) only comprises biocompatible or biodegradable material, or does not comprise any material that is not biocompatible or biodegradable.

In some embodiments, the present nanoparticle comprises: a) an interior compartment (or an inner core) that is isotonic to a cellular or physiological liquid, e.g., an interior compartment (or an inner core) comprising a liquid that is isotonic to a cellular or physiological liquid; or b) an outer surface (or shell) comprising a cellular membrane derived from a cell, said cellular membrane of said outer surface (or shell) comprising an enhanced or enriched level of a steroid. Exemplary cellular membrane can be derived from a red blood cell, a white blood cell, a platelet, a tumor cell, a cancer cell, an immune cell, a stem cell, an endothelial cell, or an epithelial cell. In some embodiments, the cellular membrane in the outer surface (or shell) does not comprise an enhanced or enriched level of a steroid, e.g., a cellular membrane derived from a red blood cell, a white blood cell, a platelet, a tumor cell, a cancer cell, an immune cell, a stem cell, an endothelial cell, or an epithelial cell that does not comprise an enhanced or enriched level of a steroid.

In some embodiments, the present nanoparticle comprises: a) an interior compartment (or an inner core) that is isotonic to a cellular or physiological liquid, e.g., an interior compartment (or an inner core) comprising a liquid that is isotonic to a cellular or physiological liquid; and b) an outer surface (or shell) comprising a cellular membrane derived from a cell, said cellular membrane of said outer surface (or shell) comprising an enhanced or enriched level of a steroid. Exemplary cellular membrane can be derived from a red blood cell, a white blood cell, cell, a platelet, a tumor cell, a cancer cell, an immune cell, a stem cell, an endothelial cell, or an epithelial cell.

In some embodiments, the interior compartment (or inner core) comprises sorbitol and the outer surface (or shell) comprises a plasma membrane derived from a red blood cell.

The present nanoparticle can have any suitable half-life in vivo. For example, the present nanoparticle can have a half-life in blood circulation in vivo for at least about 1 minute, 5 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours or longer.

In some embodiments, the nanoparticle substantially lacks immunogenicity to a subject, a mammal, a non-human mammal or a human, to which the nanoparticle is configured to administer. For example, the cellular membrane can be derived from a cell, e.g., a red blood cell, from the same species of the subject. In another example, the subject is a human and the cellular membrane is derived from a human cell, e.g., a human red blood cell. In some embodiments, the cellular membrane can be derived from a cell, e.g., a red blood cell, of the subject to be treated. For example, the cellular membrane can be derived from a red blood cell of the human to be treated.

The outer surface of the present nanoparticle can comprise a hybrid membrane comprising a cellular membrane derived from a cell and a synthetic membrane. In some embodiments, the outer surface of the nanoparticle can comprise a hybrid membrane comprising at least about 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w) of a cellular membrane. In other embodiments, the outer surface of the nanoparticle can comprise a hybrid membrane comprising at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w) of a synthetic membrane. For example, the outer surface of the nanoparticle can comprise a hybrid membrane comprising about 5-10% (w/w) of a cellular membrane and about 95-99% (w/w) of a synthetic membrane, about 11-25% (w/w) of a cellular membrane and about 75-89% (w/w) of a synthetic membrane, about 50% (w/w) of a cellular membrane and about 50% (w/w) of a synthetic membrane, about 51-75% (w/w) of a cellular membrane and about 49-25%

(w/w) of a synthetic membrane, or about 90-99% (w/w) of a cellular membrane and about 1-10% (w/w) of a synthetic membrane.

In some embodiments, the outer surface (or shell) of the present nanoparticle can further comprise a sphingolipid. The outer surface (or shell) of the present nanoparticle can comprise any suitable sphingolipid. For example, the sphingolipid can be a simple sphingolipid. In another example, the sphingolipid can be a complex sphingolipid, e.g., a sphingomyelin, a glycosphingolipid or an inositol-containing ceramide.

In some embodiments, the outer surface (or shell) of the present nanoparticle can comprise a fused cellular membrane derived a cell, steroid, e.g., cholesterol, and a sphingolipid, e.g., sphingomyelin. In some embodiments, the outer surface (or shell) of the present nanoparticle can comprise a fused plasma membrane derived a cell, steroid, e.g., cholesterol, and a sphingolipid, e.g., sphingomyelin. In some embodiments, the outer surface (or shell) of the present nanoparticle can comprise a fused plasma membrane derived a red blood cell, steroid, e.g., cholesterol, and a sphingolipid, e.g., sphingomyelin.

In another aspect or embodiment, the present disclosure provides a nanoparticle comprising an interior compartment (or an inner core) and an outer surface (or shell), wherein said interior compartment (or an inner core) does not provide a solid support to said outer surface (or shell) and/or is isotonic to a cellular or physiological liquid, e.g., an interior compartment (or an inner core) comprising a liquid that is isotonic to a cellular or physiological liquid, and said outer surface (or shell) comprises a cellular membrane derived a cell, cholesterol and sphingomyelin.

In some embodiments, the outer surface (or shell) comprises fused cellular membrane derived a cell, cholesterol and sphingomyelin. For example, the outer surface (or shell) can comprise fused plasma membrane derived a red blood cell, cholesterol and sphingomyelin.

The outer surface (or shell) can comprise any suitable level of cellular membrane derived a cell, cholesterol and sphingomyelin. For example, the outer surface (or shell) can comprise from about 20% (w/w) to about 50% (w/w) cholesterol, from about 20% (w/w) to about 80% (w/w) sphingomyelin and from about 10% (w/w) to about 50% (w/w) cellular membrane derived a cell, e.g., plasma membrane derived from a red blood cell. The about 20% (w/w) to about 50% (w/w) cholesterol level refers to a cholesterol level that is independent from (or does not include) the cholesterol level in the cellular membrane. Similarly, about 20% (w/w) to about 80% (w/w) sphingomyelin level refers to a sphingomyelin level that is independent from (or does not include) the sphingomyelin level in the cellular membrane.

In some embodiments, the outer surface (or shell) comprises about 20% (w/w), 30% (w/w), 40% (w/w), 50% (w/w) cholesterol, or a subrange thereof. In some embodiments, the outer surface (or shell) comprises about 20% (w/w), 30% (w/w), 40% (w/w), 50% (w/w), 60% (w/w), 70% (w/w), 80% (w/w) sphingomyelin, or a subrange thereof. In some embodiments, the outer surface (or shell) comprises about 10% (w/w), 20% (w/w), 30% (w/w), 40% (w/w), 50% (w/w) cellular membrane derived a cell, e.g., plasma membrane derived from a red blood cell, or a subrange thereof. In some embodiments, the outer surface (or shell) comprises about 40% (w/w) cholesterol, about 40% (w/w) sphingomyelin and about 20% (w/w) cellular membrane derived a cell, e.g., plasma membrane derived from a red blood cell.

In some embodiments, the present nanoparticle has a better stability compared to a comparable nanoparticle without the enhanced or enriched level of a steroid.

In some embodiments, the present nanoparticle is configured for binding to a type of a cell from which the cellular membrane of the nanoparticle is derived.

In some embodiments, the present nanoparticle is configured for binding or neutralizing a moiety that targets or binds to the cellular membrane of the nanoparticle. The present nanoparticle can be configured for binding or neutralizing any suitable moiety. Exemplary moiety can be an agent, e.g., a chemical agent, a molecule or an organism.

In some embodiments, the present nanoparticle is configured for binding or neutralizing a toxin, a cytokine, an autoantibody, or a chemokine that targets or binds to the cellular membrane of the nanoparticle. Exemplary toxin can be a bacterial, a fungal, an animal or a chemical toxin. Exemplary chemical toxin can be an organophosphate. Exemplary animal toxin can be a toxin in an animal venom.

In some embodiments, the "toxin" refers to a toxic material or product of plants, animals, microorganisms (including, but not limited to, bacteria, virus, fungi, rickettsiae or protozoa), or infectious substances, or a recombinant or synthesized molecule, whatever their origin and method of production. In certain embodiment, the "toxin" includes a bacterial, fungal, or animal toxin that produced within living cells or organisms. See e.g., US 2013/337066 A1 paragraphs [0131]-[0134].

In certain embodiments, the bacterial toxin includes exotoxin and endotoxin. As used herein, "exotoxins" are generated by the bacteria and actively secreted, while "endotoxins" are part of the bacteria itself (e.g., bacterial outer membrane), and it is not released until the bacteria is killed by the immune system. The present invention contemplates any exotoxin and endotoxin now known and later discovered. The type of bacterial toxin inserted in the cellular membrane is not particularly limited. In certain embodiments, the bacterial toxin is a cell membrane inserting toxin from *S. aureus*, such as alpha-hemolysin. In certain embodiments, the bacterial toxins include exotoxins secreted by *clostridium, streptococcus, listeria, bacillus*, such as pneumolysin from *Streptococcus pneumoniae*, streptolysin, e.g., streptolysin O (SLO), and streptolysin S (SLS), from *Streptococcus pyogenes*.

The present disclosure further contemplates any fungal toxins now known and later discovered, including but not limited to, aflatoxin, citrinin, ergotamine, fumonisins, ergovaline, ochratoxin, phomopsin, slaframine, sporidesmin, trichothecenes (e.g., satratoxin, deoxynivalenivalenol), zearalenone. The type of fungal toxin inserted in the cellular membrane is not particularly limited.

The animal toxins contemplated in the present disclosure includes any poison substances produced by an animal. Examples of animal toxins include, but are not limited to, cardiovascular toxins, gastrointestinal toxins respiratory toxin, neurological toxins, kidney/organ failure toxins. The present disclosure contemplates any animal toxins now known and later discovered, and the type of animal toxin inserted in the cellular membrane is not particularly limited. In certain embodiments, the animal toxin inserting into the cell membrane is from an arthropod such as the insects, arachnids and crustaceans or a reptile such as *crocodilia, rhynchocephalia, squamata* (including lizards and snakes) and testudines.

Exemplary chemical toxin include acetylcholinesterase (ACNE) inhibitors such as organophosphate poisoning. See e.g., WO 2016/176041 A1 and US 2018/0140558 A1. Exemplary organophosphates or organophosphate poisons include acephate (Orthene), aspon, Azinphos-Methyl (Guthion), Carbofuran (Furadan, F formulation), Carbophenothion (Trithion), Chlorfenvinphos (Birlane), Chlorpyrifos (Dursban, Lorsban), Coumaphos (Co-Ral), crotoxyphos (Ciodrin, Ciovap), crufomate (Ruelene), Demeton (Systox), Diazinon (Spectracide), dichlorvos (DDVP, Vapona), dicrotophos (Bidrin), Dimethoate (Cygon, De-Fend), dioxathion (Delnav), Disulfoton (Di-Syston), EPN, Ethion, Ethoprop (Mocap), famphur, fenamiphos (Nemacur), Fenitrothion (Sumithion) fensulfothion (Dasanit) fenthion (Baytex, Tiguvon), Fonofos (Dyfonate), isofenfos (Oftanol, Amaze), Malathion (Cythion), Methamidophos (Monitor), methidathion (Supracide), methyl parathion, Mevinphos (Phosdrin), Monocrotophos, Naled (Dibrom), Nerve Agents (Sarin, soman, soman, VX), oxydemeton-methyl(Meta systox-R), Parathion (Niran, Phoskil), Phorate (Thimet), phosalone (Zolonc), phosmet (Imidan, Prolate), Phosphamidon (Dimecron), temephos (Abate), TEPP, Terbufos (Counter), tetrachlorvinphos (Rabon, Ravap) and Trichlorfon (Dylox, Neguvon). The present nanoparticles can be used for decreasing or neutralizing the effect of the above organophosphates or an organophosphate poison in a subject.

In some embodiments, the present nanoparticle is configured for binding or neutralizing a bacterial, a fungus or a parasite that targets or binds to the cellular membrane of the nanoparticle.

In some embodiments, the present nanoparticle has a better ability for binding or neutralizing a moiety that targets or binds to the cellular membrane of the nanoparticle compared to a comparable nanoparticle without the enhanced or enriched level of a steroid.

In another aspect, the present disclosure provides for a medicament delivery system or device, which comprises an effective amount of the above-described nanoparticle. The medicament delivery system or device can further comprises another active ingredient, or a medically or pharmaceutically acceptable carrier or excipient.

In still another aspect, the present disclosure provides for a pharmaceutical composition comprising an effective amount of the above-described nanoparticle and a pharmaceutically acceptable carrier or excipient. The pharmaceutical composition can further comprise another active ingredient.

The pharmaceutical composition can be configured for treating or preventing a disease or condition associated with a moiety that targets or binds to the cellular membrane of the nanoparticle. In some embodiments, the outer surface of the present nanoparticle can comprise a plasma membrane derived from a blood cell, e.g., a red blood cell, a white blood cell and/or a platelet.

C. Processes for Making Nanoparticles

In yet another aspect, the present disclosure provides for a process for making a nanoparticle comprising: a) contacting a cellular membrane derived from a cell with a steroid to form a combination; and b) exerting exogenous energy on said combination in a liquid to form a nanoparticle comprising an interior compartment (or an inner core) and an outer surface (or shell) comprising said cellular membrane comprising an enhanced or enriched level of said steroid. In some embodiments, the step b) comprises exerting exogenous energy on the combination in a liquid that is isotonic to a cellular or physiological liquid to form a nanoparticle comprising an interior compartment (or an inner core) comprising the liquid that is isotonic to a cellular or physiological liquid and an outer surface comprising the cellular membrane comprising an enhanced or enriched level of the steroid.

In yet another aspect, the present disclosure provides for a process for making a nanoparticle comprising: a) contacting a cellular membrane derived from a cell with a steroid to form a combination; and b) exerting exogenous energy on said combination to form a nanoparticle comprising an interior compartment (or an inner core) and an outer surface comprising said cellular membrane comprising an enhanced or enriched level of said steroid; and c) exerting exogenous energy on said nanoparticle in a liquid that is isotonic to a cellular or physiological liquid to form a nanoparticle comprising said interior compartment (or an inner core) comprising said liquid that is isotonic to a cellular or physiological liquid and said outer surface comprising said cellular membrane comprising said enhanced or enriched level of said steroid.

In yet another aspect, the present disclosure provides for a process for making a nanoparticle, comprising exerting exogenous energy on a cellular membrane derived from a red blood cell in a liquid that is isotonic to a cellular or physiological liquid to form a nanoparticle comprising an interior compartment (or an inner core) comprising said liquid that is isotonic to a cellular or physiological liquid and an outer surface comprising said cellular membrane. In some embodiments, the process comprises the steps: a) contacting a cellular membrane derived from a red blood cell with a steroid to form a combination; and b) exerting exogenous energy on said combination in a liquid that is isotonic to a cellular or physiological liquid to form a nanoparticle comprising an interior compartment (or an inner core) comprising said liquid that is isotonic to a cellular or physiological liquid and an outer surface comprising said cellular membrane comprising an enhanced or enriched level of said steroid. In other embodiments, the process comprises the steps: a) contacting a cellular membrane derived from a red blood cell with a steroid to form a combination; b) exerting exogenous energy on said combination to form a nanoparticle comprising an inner core and an outer surface comprising said cellular membrane comprising an enhanced or enriched level of said steroid; and c) exerting exogenous energy on said nanoparticle in a liquid that is isotonic to a cellular or physiological liquid to form a nanoparticle comprising an interior compartment (or an inner core) comprising said liquid that is isotonic to a cellular or physiological liquid and an outer surface comprising said cellular membrane comprising an enhanced or enriched level of said steroid.

In yet another aspect, the present disclosure provides for a process for making a nanoparticle, comprising: a) contacting a cellular membrane derived from a cell with a steroid and a sphingolipid dissolved in a water-miscible solvent to form a combination, e.g., a combination in a liquid; and b) exerting exogenous energy on said combination or combination in a liquid to form a nanoparticle comprising an interior compartment (or an inner core) and an outer surface (or shell) comprising said cellular membrane, said steroid and said sphingolipid.

The cellular membrane used in the present process or in the present nanoparticle can be any suitable cellular membrane or be derived from any suitable cell. See e.g., above paragraphs 68-70. For example, the cellular membrane can be derived from an animal cell, e.g., a non-human mammalian cell or a human cell. In some embodiments, the cellular membrane is derived from a blood cell, a tumor cell, a cancer cell, an immune cell, a stem cell, an endothelial cell, or an epithelial cell. In some embodiments, the cellular membrane comprises a plasma membrane derived from a cell or blood cell, e.g., a red blood cell, a white blood cell and/or a platelet.

In the present process, the cellular membrane can be contained in any suitable liquid or aqueous liquid. For example, the aqueous liquid can be water, a buffer having a pH ranging from about 5 to about 9, e.g., PBS, or an isotonic liquid or buffer, e.g., 1×PBS. Any suitable buffer can be used. In some embodiments, the buffer can have a pH at about 5, 6, 7, 8, 9, or a subrange thereof.

The steroid used in the present process or in the present nanoparticle can be any suitable steroid. See e.g., above paragraphs 71-80. For example, the steroid can be a cholestane, e.g., cholesterol, a cholane, e.g., cholic acid, a pregnane, e.g., progesterone, an androstane, e.g., testosterone, or an estrane, e.g., estradiol. In another example, the steroid can be a gonane, testosterone, cholic acid, dexamethasone, lanosterol, progesterone, medrogestone, β-sitosterol, cholesterol and 5α-cholestane.

The sphingolipid used in the present process or in the present nanoparticle can be any suitable sphingolipid. See e.g., above paragraph 100. For example, the sphingolipid can be a simple sphingolipid. In another example, the sphingolipid can be a complex sphingolipid, e.g., a sphingomyelin, a glycosphingolipid or an inositol-containing ceramide.

In some embodiments, the steroid, e.g., cholesterol, and the sphingolipid, sphingomyelin, can be dissolved in the same water-miscible solvent. In some embodiments, the steroid, e.g., cholesterol, and the sphingolipid, sphingomyelin, can be dissolved in different water-miscible solvents.

The dissolution of the steroid and/or the sphingolipid in the water-miscible solvent can be facilitated by any suitable procedure or means. For example, the dissolution of the steroid and/or the sphingolipid in the water-miscible solvent can be facilitated by heating and/or mixing, e.g., stirring. In some embodiments, the heating is conducted at a temperature ranging from about 35° C. to about 65° C., e.g., at about 35° C., 40° C., 45° C., 50° C., 55° C., 60° C., 65° C., or a subrange thereof.

Any suitable water-miscible solvent can be used in the present process. For example, the water-miscible solvent can be an organic compound. Any suitable organic compound can be used. For example, the organic compound can be an alcohol, e.g., a $C_1$-$C_5$ alcohol. In some embodiments, the alcohol is methanol, ethanol, 1-propanol, 1,3-propanediol, 1,5-pentanediol, or isopropyl alcohol (isopropanol or IPA). In some embodiments, the water-miscible solvent can be one or more organic compound(s) selected from acetaldehyde, acetic acid, acetone, acetonitrile, 1,2-butanediol, 1,3-butanediol, 1,4-butanediol, 2-butoxyethanol, butyric acid, diethanolamine, diethylenetriamine, dimethylformamide, dimethoxyethane, dimethyl sulfoxide (DMSO), 1,4-dioxane, ethanol, ethylamine, ethylene glycol, formic acid, furfuryl alcohol, glycerol, methanol, methyl diethanolamine, methyl isocyanide, N-methyl-2-pyrrolidone (NMP), 1-propanol, 1,3-propanediol, 1,5-pentanediol, isopropyl alcohol, propionic acid, propylene glycol, pyridine, tetrahydrofuran (THF) or triethylene glycol.

In another example, the water-miscible solvent can be an inorganic compound. In some embodiments, the water-miscible solvent can be one or more inorganic compound(s) selected from 1,2-dimethylhydrazine, unsymmetrical dimethylhydrazine, hydrazine, hydrofluoric acid, hydrogen peroxide, nitric acid, or sulfuric acid.

In the combination, the water-miscible solvent, e.g., IPA, can have any suitable concentration or level. For example, in the combination, the water-miscible solvent, e.g., IPA, can have a concentration or level ranging from about 5% (v/v) to about 40% (v/v), e.g., at about 5% (v/v), 10% (v/v), 15% (v/v), 20% (v/v), 25% (v/v), 30% (v/v), 35% (v/v), 40% (v/v), or a subrange thereof.

The combination can have any suitable mass concentration. For example, the combination can have any suitable mass concentration ranging from about 0.25 mg/ml to about 20 mg/ml, e.g., at about 0.25 mg/ml, 0.5 mg/ml, 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 6 mg/ml, 7 mg/ml, 8 mg/ml, 9 mg/ml, 10 mg/ml, 15 mg/ml, 20 mg/ml, or a subrange thereof.

In the combination, the steroid, e.g., cholesterol, can have any suitable concentration or level. For example, in the combination, the steroid, e.g., cholesterol, can have a concentration or level ranging from about 20% (w/w) to about 50% (w/w), e.g., at about 20% (w/w), 25% (w/w), 30% (w/w), 35% (w/w), 40% (w/w), 45% (w/w), 50% (w/w), or a subrange thereof. The about 20% (w/w) to about 50% (w/w) steroid, e.g., cholesterol, level refers to a steroid, e.g., cholesterol, level that is independent from (or does not include) the steroid, e.g., cholesterol, level in the cellular membrane.

In the combination, the sphingolipid, e.g., sphingomyelin, can have any suitable concentration or level. For example, in the combination, the sphingolipid, e.g., sphingomyelin, can have a concentration or level ranging from about 20% (w/w) to about 90% (w/w), e.g., at about 20% (w/w), 25% (w/w), 30% (w/w), 35% (w/w), 40% (w/w), 45% (w/w), 50% (w/w), 55% (w/w), 60% (w/w), 65% (w/w), 70% (w/w), 75% (w/w), 80% (w/w), 85% (w/w), 90% (w/w), or a subrange thereof. The about 20% (w/w) to about 90% (w/w) sphingolipid, e.g., sphingomyelin, level refers to a sphingolipid, sphingomyelin, level that is independent from (or does not include) the sphingolipid, e.g., sphingomyelin, level in the cellular membrane.

In the combination, the cellular membrane, e.g., plasma membrane derived from a blood cell such as a red blood cell, a white blood cell and/or a platelet, can have any suitable concentration or level. For example, in the combination, the cellular membrane, e.g., plasma membrane derived from a blood cell such as a red blood cell, a white blood cell and/or a platelet, can have a concentration or level ranging from about 5% (w/w) to about 50% (w/w), e.g., at about 5% (w/w), 10% (w/w), 15% (w/w), 20% (w/w), 25% (w/w), 30% (w/w), 35% (w/w), 40% (w/w), 45% (w/w), 50% (w/w), or a subrange thereof.

In the present process, exogenous energy can be exerted on the combination using any suitable device, procedure or means. For example, in the present process, exerting exogenous energy on the combination can comprise subjecting the combination to sonication in a liquid.

In the present process, the combination can be subjected to sonication at any suitable temperature. For example, the combination can be subjected to sonication at a temperature ranging from about 15° C. to about 50° C., e.g., at about 15° C., 20° C., 25° C., 30° C., 35° C., 40° C., 45° C., 50° C., or a subrange thereof.

In the present process, the combination can be subjected to sonication at any suitable frequency. For example, the combination can be subjected to sonication at a frequency ranging from about 20 kilohertz (kHz) to about 60 kHz, e.g., at about 20 kHz, 30 kHz, 40 kHz, 50 kHz, 60 kHz, or a subrange thereof.

In the present process, the combination can be subjected to sonication for any suitable time. For example, the combination can be subjected to sonication for a time ranging from about 5 minutes to about 50 minutes, e.g., for about 5 minutes, 10 minutes, 15 minutes, 20 minutes, 25 minutes, 30 minutes, 35 minutes, 40 minutes, 45 minutes, 50 minutes, or a subrange thereof.

In the present process, exogenous energy can be exerted on the combination for any suitable purpose. For example, exerting exogenous energy on the combination, e.g., subjecting the combination to sonication, can be conducted to homogenize the cellular membrane, steroid and sphingolipid in the combination.

The present process can be used to generate any suitable nanoparticle(s). For example, the present process can be used to generate nanoparticle(s) wherein the outer surface (or shell) comprises the fused cellular membrane, steroid and sphingolipid in the nanoparticle(s).

The nanoparticles made or prepared by the present process can have any suitable size distribution. For example, the nanoparticles made or prepared by the present process can have a particle distribution index (PDI) at about 0.2 or higher, e.g., about 0.3 or higher.

The present process can further comprise, after step b), subjecting the nanoparticle(s) to a high shear treatment (or high shear force treatment) in a high shear fluid processor. Any suitable high shear fluid processor can be used. For example, the high shear fluid processor can be a microfluidizer (or a microfluidizer processor) or a homogenizer that generates high shear force.

In some embodiments, the high shear fluid processor used in the present process is a microfluidizer (or a microfluidizer processor). Any suitable microfluidizer (or a microfluidizer processor) can be used. In some embodiments, the microfluidizer is configured to generate a substantially constant pressure from about 10,000 psi to about 30,000 psi, e.g., at about 10,000 psi, 15,000 psi, 20,000 psi, at about 25,000 psi, 30,000 psi, or a subrange thereof.

In some embodiments, the microfluidizer has the microfluidics reaction technology (MRT) configuration that comprises, from upstream to downstream, an inlet for inputting the nanoparticle, an intensifier pump for generating a static pressure, an impinging jet chamber for generating a high shear pressure on the nanoparticle, and an outlet for outputting the nanoparticle. In some embodiments, the microfluidizer comprises a Z-type of interaction chamber. In some embodiments, the microfluidizer comprises a Y-type of interaction chamber.

The microfluidization can be conducted using any suitable number of pressure(s). For example, the microfluidization can be conducted using a single pressure. In another example, the microfluidization can be conducted using a combination of different pressures. The microfluidization can also be conducted using any suitable number of pass(es). For example, the microfluidization can be conducted using a single pass number. In another example, the microfluidization can be conducted using multiple passes numbers.

The present process can further comprise cooling the nanoparticle(s). In some embodiments, the nanoparticles in a channel after exiting a chamber of the microfluidizer are cooled by a product chiller that contains a coolant. The product chiller or the coolant in the product chiller can be set at any suitable temperature. For example, the product chiller or the coolant in the product chiller can be set at a temperature ranging from about 4° C. to about 55° C., e.g., at about 4° C., 5° C., 10° C., 15° C., 20° C., 25° C., 30° C., 35° C., 40° C., 45° C., 50° C., 55° C., or a subrange thereof.

The present process can be used to generate nanoparticles with any suitable size and/or size distribution. In general, nanoparticles generated with a high shear treatment (or high shear force treatment), as compared with nanoparticles generated without the high shear treatment (or high shear force treatment), have smaller sizes and a smaller range of size distribution. In some embodiments, nanoparticles generated with a high shear treatment (or high shear force treatment) have a particle distribution index (PDI) ranging from about 0.05 to about 0.2, e.g., with a PDI of about 0.05, 0.06, 0.07, 0.08, 0.09, 0.1, 0.11, 0.12, 0.13, 0.14, 0.15, 0.16, 0.17, 0.18, 0.19, 0.2, or a subrange thereof. In some embodiments, nanoparticles generated with a high shear treatment (or high shear force treatment) have a particle size having a Z-average ranging from about 30 nm to about 300 nm, e.g., with a Z-average of about 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 200 nm or a subrange thereof.

The present process can further comprise one or more of the following: 1) a step of removing or reducing the level of particles having a particle size at about 200 nm, 210 nm, 220 nm, 230 nm, 240 nm, 250 nm or larger; 2) a step of removing or reducing the level of the water-miscible solvent; 3) a step of concentrating the nanoparticles; 4) a step of sterilizing the nanoparticles; and/or 5) a step of filling the nanoparticles into individual containers. In some embodiments, the present process can further comprise 2, 3 4, or 5 of the following: 1) a step of removing or reducing the level of particles having a particle size at about 200 nm, 210 nm, 220 nm, 230 nm, 240 nm, 250 nm or larger; 2) a step of removing or reducing the level of the water-miscible solvent; 3) a step of concentrating the nanoparticles; 4) a step of sterilizing the nanoparticles; and/or 5) a step of filling the nanoparticles into individual containers.

The step of removing or reducing the level of particles having a particle size at about 200 nm, 210 nm, 220 nm, 230 nm, 240 nm, 250 nm or larger can be conducted using any suitable device, procedure or means. For example, step 1) can comprise subjecting a liquid that contains the nanoparticles to filtration. Any suitable type filtration or filter can be used. In some embodiments, the filtration can be conducted using a filter that comprises polyethersulfone (PES), polyvinylidene difluoride (PVDF), glass fiber, cellulose acetate or a combination thereof. The filter can have any suitable pore size. For example, the filter can have a pore size ranging from about 0.2 μm to about 1.2 μm, e.g., at about 0.2 μm, 0.3 μm, 0.4 μm, 0.5 μm, 0.6 μm, 0.7 μm, 0.8 μm, 0.9 μm, 1.0 μm, 1.1 μm, 1.2 μm, or a subrange thereof. In some embodiments, the filtration is conducted using a single filter. In some embodiments, the filtration is conducted using multiple filters with different pore sizes. In some embodiments, the filtration is conducted to remove or reduce the level of particles having a particle size at about 200 nm, 210 nm, 220 nm, 230 nm, 240 nm, 250 nm or larger, and to sterilize the nanoparticles.

The step of removing or reducing the level of the water-miscible solvent and/or the step of concentrating the nanoparticles can be conducted using any suitable device, procedure or means. For example, step 2) and/or 3) can comprise subjecting a liquid that contains the nanoparticles to tangential flow filtration (TFF).

The TFF can be conducted using any suitable TFF device or system. For example, TFF can be conducted using a TFF system that comprises a feed reservoir, a filter device and a collection device, the feed reservoir is in fluid communication with the filter device via an inlet on the filter device, the filter device is in fluid communication with the collection device via a permeate outlet on the filter device, and the filter device is in fluid communication with the feed reservoir via a retentate outlet on the filter device.

The filter device can be in any suitable form. For example, the filter device can be in a form of a cartridge, a cassette, or a column containing a hollow fiber filter. The filter device can comprise a filtration membrane having any suitable pore size. For example, the filter device can comprise a filtration membrane having a pore size ranging from about 100 Kd to about 300 Kd, e.g., at about 100 Kd, 150 Kd, 200 Kd, 250 Kd, 300 Kd, or a subrange thereof.

The TFF can be conducted via any suitable type of process. For example, the TFF can be conducted via a diafiltration process. In some embodiments, the diafiltration process is a continuous, discontinuous, or sequential diafiltration process. The TFF can be conducted via any suitable number of cycle(s). In some embodiments, the TFF is conducted via a single cycle. In some embodiments, the TFF is conducted via multiple cycles of diafiltration processes, e.g., multiple cycles of continuous diafiltration processes.

The present process or the TFF can further comprise collecting the nanoparticle(s). The nanoparticle(s) can be collected using any suitable device, procedure or means. For example, the nanoparticle(s) can be collected via a retentate outlet on the filter device.

The TFF can be conducted for any suitable purpose(s). In some embodiments, the TFF is used to reduce the amount or level of the water-miscible solvent from a composition, e.g., a liquid, that contains the nanoparticle. In some embodiments, the TFF is used to remove the water-miscible solvent from a composition, e.g., a liquid, that contains the nanoparticle. In some embodiments, the TFF is used to remove from about 50% to about 99.9999% of the water-miscible solvent from the composition, e.g., to remove about 50%, 60%, 70%, 80%, 90%, 95%, 99%, 99.9%99.99%99.999%, or 99.9999% of the water-miscible solvent from the composition. In some embodiments, the water-miscible solvent used in the present process is IPA and the TFF is used to reduce the IPA concentration or level below 5,000 ppm in the composition, e.g., to reduce the IPA concentration or level below 5,000 ppm, 4,000 ppm, 3,000 ppm, 2,000 ppm, 1,000 ppm, or 500 ppm in the composition.

The TFF can also be used to concentrate and/or enrich the nanoparticle(s). In some embodiments, the TFF is used to concentrate and/or enrich the nanoparticle(s) from about 1 fold to about 400 folds, e.g., to concentrate and/or enrich the nanoparticle(s) by 1 fold, 2 folds, 5 folds, 10 folds, 50 folds, 100 folds, 200 folds, 300 folds, 400 folds, or a subrange thereof.

The step of removing or reducing the level of the water-miscible solvent and the step of concentrating the nanoparticles can be conducted as a combined step or as separate steps. For example, steps 2) and 3) can be combined into a single step that comprises subjecting a liquid that contains the nanoparticles to tangential flow filtration (TFF).

The present process can further comprise a step of sterilizing the nanoparticles or a composition, e.g., a liquid, that contains the nanoparticles. For example, in the present process, before and/or after the TFF treatment, a composition, e.g., a liquid, that contains the nanoparticle is subjected to a step to sterilize the composition that contains the nanoparticle. In some embodiments, before the TFF treatment, a composition, e.g., a liquid, that contains the nanoparticle is subjected to a step to sterilize the composition that contains the nanoparticle. In some embodiments, after the TFF treatment, a composition, e.g., a liquid, that contains the nanoparticles is subjected to a step to sterilize the composition that contains the nanoparticle. In some embodiments, before and after the TFF treatment, a composition, e.g., a liquid, that contains the nanoparticle is subjected to a step to sterilize the composition that contains the nanoparticle.

The step to sterilize the composition that contains the nanoparticles can be conducted using any suitable device, procedure or means. For example, the step to sterilize the composition can comprise subjecting the composition to filtration. Any suitable type filtration or filter can be used. In some embodiments, the filtration can be conducted using a filter that comprises polyethersulfone (PES), polyvinylidene difluoride (PVDF), glass fiber, cellulose acetate or a combination thereof. The filter can have any suitable pore size. For example, the filter can have a pore size of about 0.2 µm. In some embodiments, the filtration is conducted using a single filter. In some embodiments, the filtration is conducted using multiple filters with different pore sizes.

In some embodiments, the present process does not comprise removing or vaporizing the water-miscible solvent to form a membrane comprising the steroid and the sphingolipid.

In some embodiments, the present process is conducted wherein the cellular membrane comprises a plasma membrane derived a red blood cell, the steroid is cholesterol, the sphingolipid is a sphingomyelin and the water-miscible solvent is IPA. For example, the present process can be conducted to form a nanoparticle comprising an interior compartment (or an inner core) and an outer surface (or shell) comprising said plasma membrane derived a red blood cell, cholesterol and sphingomyelin. In some embodiments, the interior compartment (or an inner core) of the nanoparticle does not providing a solid support to the outer surface (or shell). In some embodiments, the interior compartment (or inner core) of the nanoparticle is isotonic to a cellular or physiological liquid, e.g., an interior compartment (or an inner core) comprising a liquid that is isotonic to a cellular or physiological liquid. In some embodiments, the outer surface (or shell) of the nanoparticle comprises about 40% (w/w) cholesterol, about 40% (w/w) sphingomyelin and about 20% (w/w) plasma membrane derived from a red blood cell. The about 40% (w/w) cholesterol level refers to a cholesterol level that is independent from (or does not include) the cholesterol level in the cellular membrane. Similarly, about 40% (w/w) sphingomyelin level refers to a sphingomyelin level that is independent from (or does not include) the sphingomyelin level in the cellular membrane.

The cellular membrane used in the present processes can be in any suitable form. For example, the cellular membrane derived from a cell can be in a form of a cellular membrane ghost.

Any suitable exogenous energy can be used in the present processes. For example, the exogenous energy used in the present processes can be a mechanical energy, an acoustic energy, or a thermal energy.

Any suitable cellular membrane can be used in the present processes. For example, the cellular membrane used in the present processes can be derived from a mammalian or human blood cell, e.g., a red blood cell, a white blood cell, or a platelet.

Any suitable steroid can be used in the present processes. For example, the steroid used in the present processes can be a cholestane, e.g., cholesterol.

A nanoparticle prepared by the present process is also provided.

In some embodiments, the interior compartment (or an inner core) of the nanoparticle does not providing a solid support to the outer surface (or shell). In some embodiments, the interior compartment (or inner core) of the nanoparticle is isotonic to a cellular or physiological liquid, e.g., an interior compartment (or an inner core) comprising a liquid that is isotonic to a cellular or physiological liquid. In some embodiments, the interior compartment (or inner core) of the nanoparticle does not providing a solid support to the outer surface (or shell) and is isotonic to a cellular or physiological liquid, e.g., an interior compartment (or an inner core) comprising a liquid that is isotonic to a cellular or physiological liquid.

In some embodiments, the outer surface (or shell) of the nanoparticle comprises a cellular membrane derived a cell, cholesterol and sphingomyelin. In some embodiments, the outer surface (or shell) of the nanoparticle comprises a plasma membrane derived a red blood, cell, cholesterol and sphingomyelin.

In some embodiments, the outer surface (or shell) of the nanoparticle comprises fused cellular membrane derived a cell, cholesterol and sphingomyelin. In some embodiments, the outer surface (or shell) of the nanoparticle comprises fused plasma membrane derived a red blood cell, cholesterol and sphingomyelin.

In some embodiments, the outer surface (or shell) of the nanoparticle comprises from about 20% (w/w) to about 50% (w/w) cholesterol, from about 20% (w/w) to about 90% (w/w) sphingomyelin and from about 5% (w/w) to about 50% (w/w) plasma membrane derived from a red blood cell. The about 20% (w/w) to about 50% (w/w) cholesterol level refers to a cholesterol level that is independent from (or does not include) the cholesterol level in the cellular membrane. Similarly, about 20% (w/w) to about 90% (w/w) sphingomyelin level refers to a sphingomyelin level that is independent from (or does not include) the sphingomyelin level in the cellular membrane.

In some embodiments, the outer surface (or shell) of the nanoparticle comprises from about 20% (w/w) to about 50% (w/w) cholesterol, e.g., at about 20% (w/w), 25% (w/w), 30% (w/w), 35% (w/w), 40% (w/w), 45% (w/w), 50% (w/w) cholesterol, or a subrange thereof.

In some embodiments, the outer surface (or shell) of the nanoparticle comprises from about 20% (w/w) to about 90% (w/w) sphingomyelin, e.g., at about 20% (w/w), 25% (w/w), 30% (w/w), 35% (w/w), 40% (w/w), 45% (w/w), 50% (w/w), 55% (w/w), 60% (w/w), 65% (w/w), 70% (w/w), 75% (w/w), 80% (w/w), 85% (w/w), 90% (w/w) sphingomyelin, or a subrange thereof.

In some embodiments, the outer surface (or shell) of the nanoparticle comprises from about 5% (w/w) to about 50% (w/w) plasma membrane derived from a red blood cell, at about 5% (w/w), 10% (w/w), 15% (w/w), 20% (w/w), 25% (w/w), 30% (w/w), 35% (w/w), 40% (w/w), 45% (w/w), 50% (w/w) plasma membrane derived from a red blood cell, or a subrange thereof.

In some embodiments, the outer surface (or shell) of the nanoparticle comprises about 40% (w/w) cholesterol, about 40% (w/w) sphingomyelin and about 20% (w/w) plasma membrane derived from a red blood cell.

A medicament delivery system or device, which comprises an effective amount of the present nanoparticle is also provided. The medicament delivery system or device can further comprise another active ingredient, or a medically or pharmaceutically acceptable carrier or excipient.

A pharmaceutical composition comprising an effective amount of the present nanoparticle and a pharmaceutically acceptable carrier or excipient is also provided. The pharmaceutical can further comprise another active ingredient. The pharmaceutical composition can also be configured for treating or preventing a disease or condition associated with a moiety that targets or binds to the cellular membrane of the nanoparticle. The outer surface of the nanoparticle in the pharmaceutical composition can comprise any suitable cellular membrane, e.g., a plasma membrane derived from a blood cell, e.g., a red blood cell, a white blood cell and/or a platelet.

D. Methods for Treating or Preventing a Disease or Condition

In yet another aspect, the present disclosure provides for a method for treating or preventing a disease or condition in a subject in need comprising administering to said subject an effective amount of a nanoparticle comprising an interior compartment (or an inner core) and an outer surface (or shell) comprising a cellular membrane derived from a cell, said interior compartment (or an inner core) not providing a solid support to said cellular membrane in said outer surface (or shell). Optionally, and in some embodiments: a) said interior compartment (or inner core) of said nanoparticle is isotonic to a cellular or physiological liquid, e.g., an interior compartment (or an inner core) comprising a liquid that is isotonic to a cellular or physiological liquid; and/or b) said cellular membrane of said outer surface (or shell) of said nanoparticle comprises an enhanced or enriched level of a steroid. Further optionally, and in some embodiments, when the nanoparticle comprises a cellular membrane that is derived from a red blood cell, the interior compartment (or inner core) is isotonic to a cellular or physiological liquid. In some embodiments, the nanoparticle(s) is administered using a medicament delivery system or pharmaceutical composition comprising the nanoparticle(s).

The present method can be used to treat or prevent a disease or condition in any suitable subject. For example, the subject can be a human or a non-human mammal.

The nanoparticle used in the present methods can comprise any suitable cellular membrane. For example, the cellular membrane in the nanoparticle can be derived from a cell of the same species of the subject or is derived from a cell of the subject. The cellular membrane in the nanoparticle can be derived from any suitable cell. For example, the cellular membrane in the nanoparticle can be derived from a blood cell, e.g., a red blood cell, a white blood cell, and/or a platelet. In another example, the cellular membrane in the nanoparticle can be derived from a red blood cell of the same species of the subject and the red blood cell has the same blood type of the subject.

The present methods can be used for any suitable purpose. For example, the present methods can be used for treating or preventing a disease or condition associated with a moiety that targets or binds to the cellular membrane of the nanoparticle. Exemplary moiety can be an agent, e.g., a chemical agent, a molecule or an organism.

In some embodiments, the present methods can be used for treating or preventing a disease or condition associated with an organism that targets or binds to the cellular membrane of the nanoparticle. Exemplary organism can be a virus, a bacterial, a fungus or a parasite.

In some embodiments, "virus" refers to an obligate intracellular parasite of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

In some embodiments, the present methods can be used for treating or preventing a disease or condition associated with a pathogenic virus. Exemplary pathogenic viruses include smallpox virus, influenza virus, mumps virus, measles virus, chickenpox virus, ebola virus, human immunodeficiency viruses (HIV), rubella virus, hepatitis A virus (HAV), hepatitis B (HBV), hepatitis C (HCV), and hepatitis D (HDV).

In some embodiments, "bacteria" refers to small prokaryotic organisms (linear dimensions of around 1 micron) with non-compartmentalized circular DNA and ribosomes of about 70S. Bacteria protein synthesis differs from that of eukaryotes. Many anti-bacterial antibiotics interfere with bacteria proteins synthesis but do not affect the infected host. Major subdivisions of the bacteria include eubacteria and archaebacteria. In some embodiments, "eubacteria" refers to a major subdivision of the bacteria except the archaebacteria. Most Gram-positive bacteria, cyanobacteria, mycoplasmas, enterobacteria, *pseudomonas* and chloroplasts are eubacteria. The cytoplasmic membrane of eubacteria contains ester-linked lipids; there is peptidoglycan in the cell wall (if present); and no introns have been discovered in eubacteria. In some embodiments, "archaebacteria" refers to a major subdivision of the bacteria except the eubacteria. There are three main orders of archaebacteria: extreme halophiles, methanogens and sulphur-dependent extreme thermophiles. Archaebacteria differs from eubacteria in ribosomal structure, the possession (in some case) of introns, and other features including membrane composition.

In some embodiments, the present methods can be used for treating or preventing a disease or condition associated with a pathogenic bacterium. Exemplary pathogenic bacteria include bacteria causing or associated with tuberculosis (TB), e.g., *Mycobacterium tuberculosis* (M. tb), pneumonia, e.g. *Streptococcus* or *Pseudomonas*, foodborne illness, e.g., *E. coli, Shigella, Campylobacter, Salmonella*, tetanus, typhoid fever, diphtheria, syphilis, and leprosy.

In some embodiments, "fungus" refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

In some embodiments, the present methods can be used for treating or preventing a disease or condition associated with a pathogenic fungus. Exemplary pathogenic fungi include *Candida albicans* which is the most common cause of Candidiasis and *Cryptococcus neoformans* which can cause a severe form of Meningitis.

In some embodiments, the present methods can be used for treating or preventing a disease or condition associated with a parasite. Exemplary human parasites include parasites that cause or are associated with malaria, leishmaniasis, cryptosporidiosis, amoebiasis, chagas disease, African trypanosomiasis, schistosomiasis, ascariasis, echinococcosis, and cysticercosis.

In some embodiments, the present methods can be used for treating or preventing a disease or condition associated with a toxin, a cytokine, an autoantibody, or a chemokine that targets or binds to the cellular membrane of the nanoparticle. Exemplary toxin can be a bacterial, a fungal, an animal or a chemical toxin. Exemplary chemical toxin can be an organophosphate. Exemplary animal toxin can be a toxin in an animal venom.

In some embodiments, the present methods can be used for treating or preventing a disease or condition associated with a cell membrane inserting toxin. In specific embodiments, the toxin inserts into the cellular membrane or plasma membrane of a target cell of the subject as part of the toxin's natural pathological mechanism. In specific embodiments, the cellular membrane or plasma membrane in the outer surface of the nanoparticle used in the present methods substantially retains the toxin. In specific embodiments, the outer surface of the nanoparticle used in the present methods comprises a plasma membrane derived from a blood cell, e.g., a red blood cell, a white blood cell, and/or a platelet.

In some embodiments, the present methods can be used for treating or preventing skin infection, sepsis, pneumonia, an autoimmune reaction, e.g., an autoimmune reaction due to production of an autoimmune antibody such as an autoimmune antibody against blood cells or red blood cells.

In some embodiments, the present methods can further comprise administering another active ingredient, or a pharmaceutically acceptable carrier or excipient to the subject in need. In some embodiments, the present nanoparticle can be administered via a medicament delivery system or device.

In some embodiments, the present methods can be used for treating or preventing infection, e.g., skin infection, sepsis, pneumonia, or an autoimmune reaction, e.g., an autoimmune reaction due to production of an autoimmune antibody such as an autoimmune antibody against blood cells or red blood cells.

The nanoparticle(s) or a composition comprising the nanoparticle(s), e.g., a pharmaceutical composition comprising the nanoparticle(s), can be administered through any suitable route or procedure. For example, the nanoparticle or a composition comprising the nanoparticle(s), e.g., a pharmaceutical composition, can be administered via enteral/gastrointestinal, oral, parenteral, intravenous, rectal, nasal, topical, ocular, inhalation or intratracheal route.

In some embodiments, the nanoparticle or a composition comprising the nanoparticle(s), e.g., a pharmaceutical composition, can be administered via intratracheal route. For example, the disease or condition to be treated or prevented can be infection, e.g., skin infection, sepsis, or pneumonia, and the nanoparticle or a composition comprising the nanoparticle(s), e.g., a pharmaceutical composition, can be administered via intratracheal route. Any suitable intratracheal administration can be used. For example, the nanoparticle or a composition comprising the nanoparticle(s), e.g., a pharmaceutical composition, can be administered via intratracheal instillation or intratracheal inhalation.

In some embodiments, the neoplasm specific immunogenic composition or vaccine can be administered via enteral/gastrointestinal, oral, parenteral, intravenous, rectal, nasal, topical, ocular, inhalation or intratracheal route.

In some embodiments, the immunogenic composition for eliciting an immune response to a moiety associated with a disease or condition in a subject can be administered via enteral/gastrointestinal, oral, parenteral, intravenous, rectal, nasal, topical, ocular, inhalation or intratracheal route.

In some embodiments, the present methods further comprise administering to the subject a second therapeutic agent, Any suitable second therapeutic agent can be used. For example, the second therapeutic agent can be an antibiotic, an anti-tumor or anti-cancer agent, or an immunresponse modulator, e.g., an immunresponse activator or suppressor.

In some embodiments, the present methods do not comprise administering to the subject a second therapeutic agent.

In yet another aspect, the present disclosure provides for an use of an effective amount of the present nanoparticle for the manufacture of a medicament for treating or preventing a disease or condition in a subject in need.

E. Immunogenic Compositions and Uses Thereof

In yet another aspect, the present disclosure provides for an immunogenic composition, which comprises an effective amount of the present nanoparticle, and optionally further comprises an immunogenic adjuvant or an immunopotentiator.

The present immunogenic composition can be configured for any suitable use for application. In some embodiments, the present immunogenic composition can be configured as a neoplasm specific immunogenic composition, and wherein the outer surface of the nanoparticle comprises a cellular membrane derived from a neoplasm cell.

The cellular membrane of the nanoparticle in the neoplasm specific immunogenic composition can be derived from any suitable neoplasm cell. For example, the cellular membrane of the nanoparticle in the neoplasm specific immunogenic composition can be derived from a benign neoplasm cell, a potentially malignant neoplasm cell, a cancer cell, a cancer cell line, or a cancer cell of a subject.

In some embodiments, the cellular membrane in the outer surface of the nanoparticle in the neoplasm specific immunogenic composition substantially retains its structural integrity for eliciting an immune response to the neoplasm cell.

In other embodiments, the interior compartment (inner core) of the nanoparticle in the neoplasm specific immunogenic composition does not support the outer surface (or shell) of the nanoparticle.

In some embodiments, the nanoparticle in the neoplasm specific immunogenic composition can further comprises another active ingredient, or a releasable cargo.

The nanoparticle in the neoplasm specific immunogenic composition can have any suitable size. For example, the nanoparticle can have a diameter from about 10 nm to about 10 μm. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm, or any sub-range within about 10 nm to about 10 μm, e.g., any range between any two of the above sizes.

In some embodiments, the nanoparticle in the neoplasm specific immunogenic composition substantially lacks constituents of the neoplasm cell from which the cellular membrane is derived. For example, the nanoparticle can lack about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the neoplasm cell from which the cellular membrane is derived.

In some embodiments, the nanoparticle in the neoplasm specific immunogenic composition substantially maintains natural structural integrity or activity of the cellular membrane or the constituents of the cellular membrane. For example, the nanoparticle can retain about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity. In some embodiments, the nanoparticle substantially maintains natural structural integrity of the cellular membrane or the constituents of the cellular membrane including primary, secondary, tertiary and/or quaternary structure of the cellular membrane, or the constituents of the cellular membrane. In some embodiments, the nanoparticle substantially maintains activity of the cellular membrane or the constituents of the cellular membrane including binding activity, receptor activity and/or enzymatic activity of the cellular membrane, or the constituents of the cellular membrane.

In some embodiments, the present neoplasm specific immunogenic composition can further comprise an immunogenic adjuvant or an immunopotentiator.

In some embodiments, the outer surface of the nanoparticle in the present neoplasm specific immunogenic composition comprises a naturally occurring cellular membrane and further comprises a synthetic membrane.

A vaccine comprising the present neoplasm specific immunogenic composition is also provided.

A method for treating or preventing a neoplasm in a subject in need comprising administering to said subject an effective amount of the present neoplasm specific immunogenic composition is also provided.

The present method can be used to treat or prevent a neoplasm in any suitable subject. For example, the subject can be a human or a non-human mammal.

The nanoparticle used in the present methods can comprise any suitable cellular membrane. For example, the cellular membrane in the nanoparticle can be derived from a cell of the same species of the subject or is derived from a neoplasm cell of the subject.

In some embodiments, the present methods can further comprise administering another active ingredient, or a pharmaceutically acceptable carrier or excipient to the subject in need. In some embodiments, the present nanoparticle can be administered via a medicament delivery system or device.

In yet another aspect, the present disclosure provides for an use of an effective amount of the present neoplasm specific immunogenic composition for the manufacture of a vaccine for treating or protecting a subject against a neoplasm.

In some embodiments, the present immunogenic composition can be configured for treating or preventing a disease or condition associated with a moiety that targets or binds to the cellular membrane of the nanoparticle, and wherein the outer surface of the nanoparticle comprises the moiety. Exemplary moiety can be an agent, e.g., a chemical agent, a molecule or an organism.

In some embodiments, the present immunogenic compositions can be used for treating or preventing a disease or condition associated with an organism that targets or binds to the cellular membrane of the nanoparticle. Exemplary organism can be a bacterial, a fungus or a parasite.

In some embodiments, the present immunogenic compositions can be used for treating or preventing a disease or condition associated with a toxin, a cytokine, an autoantibody, or a chemokine. Exemplary toxin can be a bacterial, a fungal, an animal or a chemical toxin. Exemplary chemical toxin can be an organophosphate. Exemplary animal toxin can be a toxin in an animal venom.

In some embodiments, the present immunogenic compositions can be used for treating or preventing a disease or condition associated with a cell membrane inserting toxin. In specific embodiments, the toxin inserts into the cellular membrane or plasma membrane of a target cell of the subject as part of the toxin's natural pathological mechanism. In specific embodiments, the cellular membrane or plasma membrane in the outer surface of the nanoparticle substantially retains the toxin.

The cellular membrane in the outer surface of the nanoparticle in the present immunogenic compositions can be derived from any suitable cell. In some embodiments, the cellular membrane is a plasma membrane derived from a cell. In some embodiments, the outer surface comprises a plasma membrane derived from a red blood cell.

In some embodiments, the outer surface of the nanoparticle in the present immunogenic compositions can comprise a naturally occurring cellular membrane and can further comprise a synthetic membrane.

In some embodiments, the nanoparticle in the present immunogenic compositions can be biocompatible, biodegradable, or can comprise a synthetic material.

In other embodiments, the interior compartment (inner core) of the nanoparticle in the present immunogenic composition does not support the outer surface (or shell) of the nanoparticle.

In some embodiments, the present immunogenic composition can further comprise another active ingredient or an immunogenic adjuvant or immunopotentiator.

A vaccine which comprises the present immunogenic composition is also provided.

A method for eliciting an immune response to a moiety associated with a disease or condition in a subject is also provided, which comprises administering to said subject an effective amount of the present immunogenic composition.

A method for protecting a subject against a moiety associated with a disease or condition in a subject is also provided, which comprises administering to said subject an effective amount of the present vaccine.

The present method can be used to treat or prevent a disease or condition in any suitable subject. For example, the subject can be a human or a non-human mammal.

In some embodiments, the cellular membrane or plasma membrane of the nanoparticle used in the present methods can be derived from a cell of the same species of the subject or a cell of the subject. In some embodiments, the plasma membrane is derived from a red blood cell of the same species of the subject and the red blood cell has the same blood type of the subject.

In some embodiments, the present methods can further comprise administering another active ingredient or a pharmaceutically acceptable carrier or excipient to said subject.

The present methods can be used to elicit any suitable type of immune response from a subject. In some embodiments, the present methods can be used to elicit a T-cell mediated immune response, or a B-cell mediated immune response from a subject.

In yet another aspect, the present disclosure provides for an use of an effective amount of the present immunogenic composition for the manufacture of a vaccine for protecting a subject against a disease or condition associated with the moiety.

F. Pharmaceutical Compositions and Administration Routes

The pharmaceutical compositions comprising the nanoparticles, alone or in combination with other active ingredient(s), described herein may further comprise one or more pharmaceutically-acceptable excipients. A pharmaceutically-acceptable excipient is a substance that is non-toxic and otherwise biologically suitable for administration to a subject. Such excipients facilitate administration of the nanoparticles, alone or in combination with other active ingredient(s), described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the various embodiments are sterile compositions. Pharmaceutical compositions may be prepared using compounding techniques known or that become available to those skilled in the art.

Sterile compositions are within the present disclosure, including compositions that are in accord with national and local regulations governing such compositions.

The pharmaceutical compositions and the nanoparticles, alone or in combination with other active ingredient(s), described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. The nanoparticles, alone or in combination with other active ingredient(s), described herein, and preferably in the form of a pharmaceutical composition, may be administered by a suitable route of delivery, such as oral, parenteral, rectal, nasal, topical, or ocular routes, or by inhalation. In some embodiments, the compositions are formulated for intravenous or oral administration.

For oral administration, the nanoparticles, alone or in combination with another active ingredient, may be provided in a solid form, such as a tablet or capsule, or as a solution, emulsion, or suspension. To prepare the oral compositions, the nanoparticles, alone or in combination with other active ingredient(s), may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinylpyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions may be formulated for rectal administration as a suppository. For parenteral use, including intravenous, intramuscular, intraperitoneal, intranasal, or subcutaneous routes, the nanoparticles, alone or in combination with other active ingredient(s), may be provided in sterile aqueous solutions or suspensions, buffered to an appropriate pH and isotonicity or in parenterally acceptable oil. Suitable aqueous vehicles can include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For nasal, inhaled, or oral administration, the nanoparticles, alone or in combination with other active ingredient(s), may be administered using, for example, a spray formulation also containing a suitable carrier.

For topical applications, the nanoparticles, alone or in combination with other active ingredient(s), are preferably formulated as creams or ointments or a similar vehicle suitable for topical administration. For topical administration, the nanoparticles, alone or in combination with other active ingredient(s), may be mixed with a pharmaceutical carrier at a concentration of about 0.1% to about 10% of drug to vehicle. Another mode of administering the nanoparticles, alone or in combination with other active ingredient(s), may utilize a patch formulation to effect transdermal delivery.

In certain embodiments, the present disclosure provides pharmaceutical composition comprising the nanoparticles, alone or in combination with other active ingredient(s), and methylcellulose. In certain embodiments, methylcellulose is in a suspension of about 0.1, 0.2, 0.3, 0.4, or 0.5 to about 1%. In certain embodiments, methylcellulose is in a suspension of about 0.1 to about 0.5, 0.6, 0.7, 0.8, 0.9, or 1%. In certain embodiments, methylcellulose is in a suspension of about 0.1 to about 1%. In certain embodiments, methylcellulose is in a suspension of about 0.1, 0.2, 0.3, 0.4, 0.5, 0.6, 0.7, 0.8, 0.8, or 1%. In certain embodiments, methylcellulose is in a suspension of about 0.5%.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

One of ordinary skill in the art may modify the formulations within the teachings of the specification to provide numerous formulations for a particular route of administration. In particular, the nanoparticles, alone or in combination with other active ingredient(s), may be modified to render them more soluble in water or other vehicle. It is also well within the ordinary skill of the art to modify the route of administration and dosage regimen of a particular nanoparticle, alone or in combination with other active ingredient(s), in order to manage the pharmacokinetics of the present compounds for maximum beneficial effect in a patient.

E. Examples

Aspects of the present teachings may be further understood in light of the following examples, which should not be construed as limiting the scope of the present teachings in any way.

Example 1

Formulation and Characterization of Cholesterol-Enriched Nanoparticles

Experimental Details

Cell Membrane Derivation: To derive RBC membranes devoid of cytoplasmic contents, packed RBCs of ICR mice (6-8 w, obtained from BioIVT) were washed with repeated centrifugation at 800×g for 5 min in ice cold 1×PBS at 4° C. For hypotonic treatment, the cells were then suspended in 0.25×PBS in an ice bath for 20 min and were centrifuged at 800×g for 5 min. The hemoglobin was removed, whereas the pink pellet was collected. The process was repeated three times. Membrane protein content was quantified with a Pierce BCA assay (Life Technology). To derive the membrane of mammalian cells (e.g. platelet, J774 mouse macrophages, and neutrophil-like cells induced from HL-60 cells), cells were spun down and the pellets were washed three times with 1×PBS. Then cell pellets were dispersed in an isolation buffer solution consisting of 15 mL 1×PBS, 0.5 mM ethylene glycol-bis(2-aminoethylether)-N,N,N',N'-tetraacetic acid (EGTA; Sigma), and 50 μL phosphatase inhibitor and protease inhibitor cocktails (100×, Sigma). The suspension was loaded into a dounce homogenizer and the cells were disrupted with 15 passes. Following the disruption, the suspension was spun down at 800×g for 5 min to remove large debris. The supernatant was collected and centrifuged again at 10,000×g for 25 min, after which the pellet was discarded, and the supernatant was centrifuged at 150,000×g for 35 min. After the centrifugation, the supernatant was discarded, and the plasma membrane was collected as an off-white pellet. The membrane pellet was then washed once with 1 mM ethylenediaminetetraacetic acid (EDTA; USB Corporation) in H2O, resuspended with gentle sonication for subsequent experiments. Membrane protein content was quantified with a Pierce BCA assay (Life Technology).

Formulation of Cholesterol-stabilized Membrane Vesicles: To produce cholesterol-enriched cell membrane vesicles, cholesterol (Avanti Polar Lipids) dissolved at 50 mg/mL in chloroform was added at varying initial loading to membrane ghosts, followed by gentle mixing at 37° C. for 10 minutes. To form vesicles, the suspensions were either sonicated for 6 minutes in a Fisher Scientific FS30D bath sonicator, or they were extruded sequentially through 1-μm, 400-nm, and 200-nm pore size polycarbonate membranes (Whatman) using an Avanti Polar Lipids mini extruder. To remove un-incorporated cholesterol, suspensions of membrane vesicles were added to hexane (at approximately ~1:1 volume ratio) and the mixture was placed at room temperature for 30 min.

Cholesterol Quantification: Total cholesterol content was quantified by using the Amplex® Red Cholesterol Assay Kit (ThermoFisher Scientific) based on manufacturer's instruction.

MRSA 300 Supernatant (MS) Preparation: MRSA USA300 stock (American Type Culture Collection, ATCC) was inoculated onto a tryptic soy broth (TSB) agar plate and incubated at 37° C. for 30 h. Then a single colony was transferred from the agar plate into 4 mL TSB broth, followed by incubation at 37° C. with gentle shaking for 12 h. Then, the bacterial culture was transferred to 200 mL of fresh TSB followed by culture at 37° C. for approximately 24 h until the OD600 value reached ~7 (OD600=1 corresponds to $1 \times 10^8$ CFU/mL bacteria). To collect the supernatant, bacterial culture was first centrifuged at 4,500×g for 30 min and then the supernatant was passed through a 0.2-μm membrane filter. The supernatant was then lyophilized and reconstituted to 1/10 of its volume (equivalent to a 10× concentration). Aliquots of MS were stored in −80° C. for subsequent experiments.

Neutralization of MRSA Supernatant (MS) Hemolytic Activity with Cholesterol-enriched RBC Membrane Vesicles (Cho-RBC-V): To evaluate the neutralization of MS hemolytic activity, 4.5 μL of MS was mixed with various concentrations of Cho-RBC-V first to a final volume of 60 μL in 10 w/v % of sucrose and 10 mM DTT. The mixture was incubated at 37° C. for 30 min and then added to 100 μL of 5 v/v % human RBC suspension followed by a 30 min-incubation at 37° C. After the incubation, supernatants were collected, and the released hemoglobin was quantified by measuring the absorbance at 540 nm on a plate reader. All experiments were performed in triplicate.

Neutralization of Antiplatelet Antibody with Cholesterol-enriched Platelet Membrane Vesicles (Cho-PL-V): Recombinant human TNF-α (Thermo Fisher Scientific, final concentration 8.82±0.80 ng ml$^{-1}$) was mixed with Cho-Neu-V (final concentrations 64, 128, 256, 512, and 1024 μg/mL). The mixtures were incubated for 2 h at 37° C. and then centrifuged at 16,100 g for 10 min to remove the vesicles. Cytokine concentration in the supernatant was quantified by human TNF-α enzyme-linked immunosorbent assay (ELISA) kits (Biolegend). All experiments were performed in triplicate.

Neutralization of Endotoxin with Cholesterol-enriched Macrophage Membrane Vesicles (Cho MΦ-V): To determine the neutralization of lipopolysaccharide (LPS) with Cho-MΦ-V, samples of Cho-MΦ-V (64, 128, 256, 512, and 1024 μg/mL) mixed with LPS (LPS-EK, InvivoGen, 50 microg/mL) and immediately added to J774 macrophages ($2 \times 10^4$ cells/well in 96-well tissue culture plate). Cells were cultured at 37° C. for 5 hours. Following the culture period, IL-6 concentration in the culture media was quantified by mouse IL-6 enzyme-linked immunosorbent assay (ELISA) kit (Biolegend). All experiments were performed in triplicate.

Neutralization of Inflammatory Cytokines (TNF-α) with Cholesterol-enriched Neutrophil Membrane Vesicles (Cho Neu-V): Recombinant human TNF-α (Thermo Fisher Scientific, final concentration 8.82±0.80 ng ml$^{-1}$) was mixed with Cho-Neu-V (final concentrations 64, 128, 256, 512, and 1024 μg/mL). The mixtures were incubated for 2 h at 37° C. and then filtered using 1 300 kDa MW cutoff centrifugal filter (Nanosep, Pall Laboratory) at 16,000×g for 5 min to separate unbound cytokines with vesicle-bound cytokines. Cytokine concentration in the filtrate was quantified by human TNF-α enzyme-linked immunosorbent assay (ELISA) kits (Biolegend).

FIGS. 1-4 illustrate formulation and characterization of several types of cholesterol-enriched cellular membrane vesicles, including cholesterol-enriched RBC membrane vesicles (Cho-RBC-V), cholesterol-enriched platelet membrane vesicles (Cho-PL-V), cholesterol-enriched macrophage membrane vesicles (Cho-MΦ-V) and cholesterol-enriched neutrophhil membrane vesicles (Cho-Neu-V).

Example 2

Preparation of Composition A
Experimental Design and Methods

Material and Devices

Sphingomyelin was purchased from NOF. Cholesterol was from Spectrum. Isopropyl alcohol was from Sigma Aldrich. Sterile PBS (1×) was from Hyclone. M-110EH-30 Microfluidizer was from Microfluidics International Corporation. KMPi TFF pump system was from Repligen. Cellulose Acetate (CA) capsule filter (0.2 μm) was purchased from Sartorius. Glass capsule Fiber (0.2 μm) was purchased from PALL.

hRBC membrane was prepared with tangential flow filtration (TFF) to reduce the level of hemoglobin and other impurities using the principles disclosed in WO 2017/087897 A1. Generally, lysed hRBCs are subject to dilution, concentration and diafiltration using TFF one or more times to remove hemoglobin and other impurities. The hRBC membrane in 1×PBS buffer is collected at the end of the process.

Test Methods

The nanoparticle (or nanosponge) size and distribution index (PDI) were measured through zetasizer nano series Model: ZEN 3600. The sample was diluted into 1×PBS with the measuring concentration of 0.25 mg/ml.

Procedures

Based on the starting concentration, calculate the amount for individual contents. For example, for starting concentration of 2.5 mg/ml, 2,000 ml, calculation result for each component as shown in Table 1 below.

TABLE 1

| 2.5 mg/ml, 2,000 ml | |
| --- | --- |
| SM | 2,000 mg |
| Cholesterol | 2,000 mg |
| IPA | 200 ml |
| hRBC | 1,000 mg |

Preparation of SM/Chol IPA Solution

The SM and cholesterol were weighed and added to a glass bottle. IPA was added into the SM/cholesterol bottle. The SM/Chol IPA was heated until totally dissolved.

Preparing Starting Working Mixture for Sonication hRBC membrane in 1×PBS was mixed with SM and cholesterol IPA solvent (SM:Cholesterol:hRBC membrane weight ratio equals to 4:4:2). The mixture was mixed well through vortex or stirrer bar. The mixture of hRBC membrane, SM and cholesterol was homogenized through sonication bath.

Microfluidization for Nanoparticle (or Nanosponge) Preparation

The RBC membrane/SM/cholesterol mixture after sonication was passed through the microfluidizer with 20 k psi. Nanoparticles (or nanosponges) were chilled by a product chiller and collected.

Pre-Filtration of Nanosponge

The resulting nanosponge suspension was prefiltered through a 0.45 µm Glass Fiber combining with 0.2 µm cellulose acetate sterile filter for sterilization and to remove bigger particles (>200 µm). Then, TFF (300 kd Hollow Fiber column) was used to concentrate the nanosponge and to remove IPA (below 5,000 ppm) through diafiltration.

Figure 6:
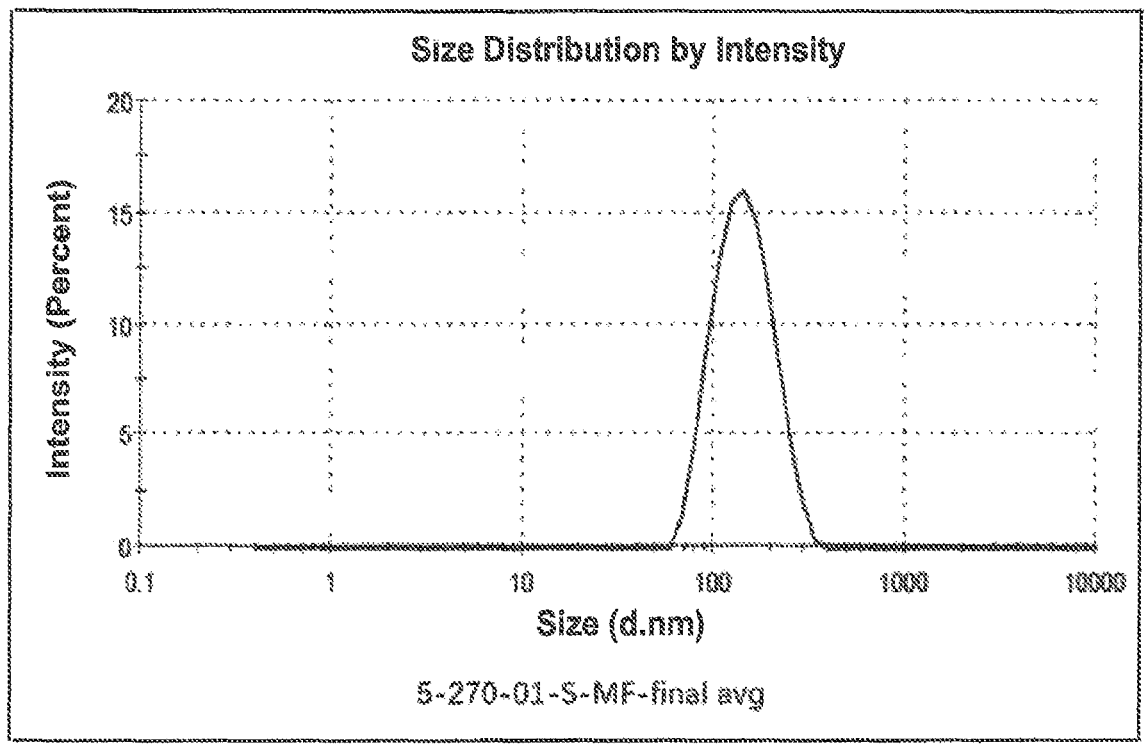

Particle size distribution of an exemplary preparation of Composition A (lot 5-270-01-S-MF-final avg) is shown in FIG. 6.

Example 3

Effects of Composition A on Survival Rate in A Murine Model of Pneumonia Infected with Methicillin-Resistant *Staphylococcus aureus* USA300

Summary

*Staphylococcus aureus* is a leading cause of pneumonia acquired in hospital or in community, with mortality rates up to 60%. Treatment of the infection is hampered by the fact that a half of *Staphylococcus aureus* isolates from patients with pneumonia are methicillin-resistant *Staphylococcus aureus* (MRSA). Vancomycin and Linezolid are currently the primary antibiotic therapies for MRSA pneumonia. However, the mortality rate in pneumonia patients treated with both remains high, and the emergence of resistance and occurrence of side effect limits the usefulness of these antibiotics. A consistent evolution toward antibiotic resistance has led to the exploration of alternate methods of prevention and treatment of MRSA pneumonia. One such approach is to target virulent factors such as pore-forming toxins produced by MRSA to prevent pulmonary inflammation and epithelial cytolysis.

In this study, we developed a murine model of lung infection caused by MRSA USA300, and used the model to evaluate the effects of intratracheal administration of Composition A, a lead formulation of hRBC nanosponges, on the survival improvement of infected mice. The results of this study show that intratracheal administration of Composition A consistently reduced the mortality of pneumonia mice infected with MRSA USA300. The survival improvement is not lot-dependent, but is a dose-dependent. At 2, 6 and 19 mg/kg, Composition A significantly improved the mouse survival rate by 38%, 66% and 68%, respectively, in comparison to that (26% survival rate) treated with vehicle. Moreover, intratracheal administration of Composition A reduced the bacterial load in the lungs of mice infected with MRSA USA300, potentially underlying the mechanisms of action of Composition A.

Materials and Methods

Animals and Husbandry

Eight week old female or male CD1 mice (24-28 grams in body weight) were purchased from Charles River Laboratories. Mice were group-housed (5/cage) in solid-bottom micro-isolator cages on stainless steel racks, and were fed irradiated Teklad Global 2918 Rodent Diet and water ad libitum. Bedding were provided in the form of irradiated Teklad ⅛" corn cob bedding 7902.

The environment was controlled to a temperature range of 74°±5° F. and a humidity range of 30-70%. Fluorescent lighting provided illumination for 12 hours per day.

Mice were acclimated for a minimum of 24 hours prior to study start. The animals were observed for general health and acceptability for use in this study. Only animals deemed healthy were included in this study. Animals were handled in accordance with IACUC procedures and were in accordance with Animal Use Protocol (AUP) number S00227m.

Bacteria, Culture and Intratracheal Instillation

Methicillin-Resistant *Staphylococcus aureus* (MRSA) USA300 (TPPS 1056) bacteria were grown overnight at 37° C. in 5% $CO_2$ atmosphere on Todd Hewitt on trypticase soy agar plates supplemented with 5% sheep blood cells. The culture was aseptically swabbed and transferred to a liquid culture in Todd Hewitt broth for overnight growth. On the day of infection, the bacteria were sub-cultured at 1:10 dilution and allowed to grow to mid-log phase at OD 600 nm of 0.4. The cultures were washed with 1× phosphate buffer saline (PBS) several times to remove bacterium-released toxins during the culture, and diluted to provide a targeted challenge inoculum in the range of $1\times10^7$-$8\times10^9$ CFU per mouse in a volume of 30 µL. Inoculum count will be estimated before inoculation by optical density and confirmed after inoculation by dilution, plating, 24-hour incubation and back count. Data is then recorded as "inoculum".

On the day of experiment, mice were anesthetized with ketamine and xylazine (90 mg/kg and 10 mg/kg intraperitoneally, respectively), and an anesthetized mouse was held to an Otoscope tip, and the glottis and vocal chords of the mouse was visualized using the Otoscope magnifying glass and light source. A 30 µL of bacteria culture was then delivered into the trachea via a long plastic pipette.

Intratracheal Administration of Composition

Immediately after bacterial instillation (<1 min) when mice were still anesthetized, 30 µL of Composition A or PBS as the vehicle was intratracheally administered via a long plastic pipette tip. Mice were allowed to recover from anesthesia and return to the home cages. The dose per animal was calculated based upon the lot concentration of Composition A used and the averaged body weight of the group animals tested.

Mortality as the Endpoint

Mice were closely observed throughout the study period for signs of morbidity and impending mortality. Survival were tracked for 4 days (unless otherwise) following bacterial challenge/nanosponge treatment. Mice surviving at the study end were humanely euthanized via $CO_2$ overexposure.

Pulmonary Bacterial Count as the Endpoint

The mice assigned for pulmonary bacterial count were allowed to live for 24 or 48 hours following bacterial challenge/nanosponge treatment. At either the time point, mice will be humanely euthanized via $CO_2$ overexposure, and the left and right lungs will be collected. The lung tissues were homogenized and plated in a 96 well plate. The plate was incubated overnight at either 30° C. or 37° C. in an incubator. The easiest-to-count dilution was counted, and dilution and counts were recorded. From this data CFU/gram tissue was calculated.

Statistical Analysis

Quantitative data were expressed as the mean±SEM. The survival data were analyzed using the Mantel-Cox Log-rank test or Gehan-Breslow-Wilcoxon test as appropriate (or unless otherwise). The CFU data were analyzed using Analysis of Variance (ANOVA) followed by Dunnett's tests or Student's t-test as appropriate. All statistical analyses were performed using GraphPad Prism version 7.01. A p value of <0.05 was considered statistically significant.

Results

Identification of Composition A

An initial screening study (007) was performed to identify a lead formulation in the mouse model of MRSA pneumonia. In this study, pneumonia was induced by intratracheal instillation of 30 μL of MRSA USA300 culture broth containing $5\times10^7$ colony forming units (CFU)/mouse. Immediately after the bacterial challenge (within 1 minute), mice (n=10 mice/group) were intratracheally dosed with Composition A or 5% sorbitol/95% phosphate buffer saline (PBS) as the vehicle. Mice were allowed to survive for 48 hours after bacterial challenge/formulation treatment. The number of mice died in each treatment group within 48 hours was counted, and analyzed for survival rate. At the 48 hour time point, the remaining survived mice were sacrificed, and the lungs were harvested and processed for CFU enumeration. The survival data are summarized in Table 2 below and shown in FIG. 7A. In the first 48 hours, 5 mice treated with the vehicle died and no mouse treated with Composition A died; the survival rate was 50% and 100%, respectively. The difference in the survival rate between vehicle and Composition A treated groups was statistically significant.

TABLE 2

Study Design and Results

| n | MRSA USA300 CFU/ mouse | Treatment | Vol (μL) | Dose (mg/kg) | Schedule | Animal Deaths/Survival Rate | | | |
|---|---|---|---|---|---|---|---|---|---|
| | | | | | | Hours Post Challenge/Treatment | | Total | % |
| | | | | | | 0-24 | 25-48 | Deaths | Survival |
| 10 | $5 \times 10^7$ | 5% sorbitol/ 95% PBS | 30 | N/A | <1 min | 3 | 2 | 5 | 50% |
| 10 | $5 \times 10^7$ | Composition A | 30 | 19 | <1 min | 0 | 0 | 0 | 100% |

Reproducible Effects of Composition A on Improving Survival Rate

Figure 8:
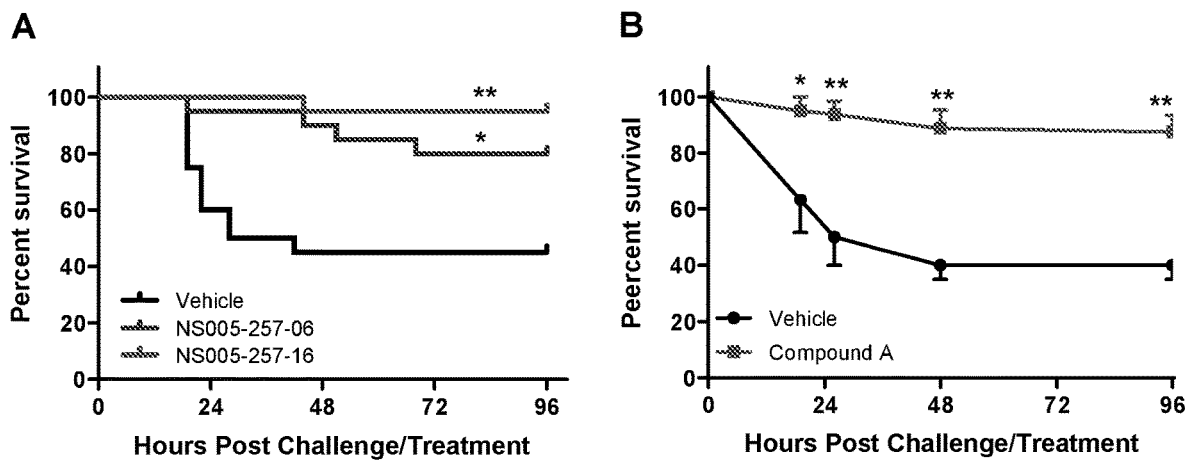

In the study above described, we demonstrated that Composition A lot 5-257-06 significantly improved the survival rate and reducing the pulmonary bacterial load in the mouse model of MRSA pneumonia. To determine reproducibility of the effect, we tested 3 different lots of Composition A with similar concentrations in the model. FIG. 8A shows an example of the tests. In this study (011), after bacterial instillation, mice were intratracheally dosed with PBS (vehicle), lot 5-257-06 at 19 mg/kg or lot 5-257-16 at 22 mg/kg, and were observed for 96 hours after treatment. As shown in FIG. 8A, at 96 hours post challenge/treatment, the survival rate in the vehicle-treated group was 55%. Treatment with lots 5-257-06 and 5-257-16 significantly improved the survival rate (to 80% and 95%, respectively). FIG. 8B plots the data of the survival rate averaged from tests with 3 different Composition A lots (5-257-06 at 19 mg/kg, 5-257-16 at 22 mg/kg and 5-260-02 at 25 mg/kg). A significant improvement of the survival rate was observed following treatments at all observation time points from 19 hours to 96 hours post challenge/treatment.

Dose-Curve Study of Composition A

Figure 9:
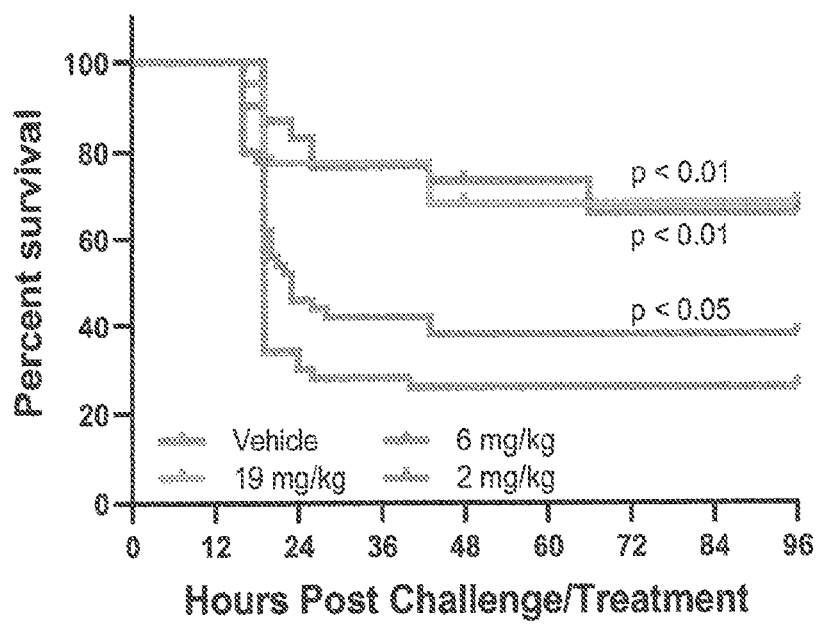
Figure 10:
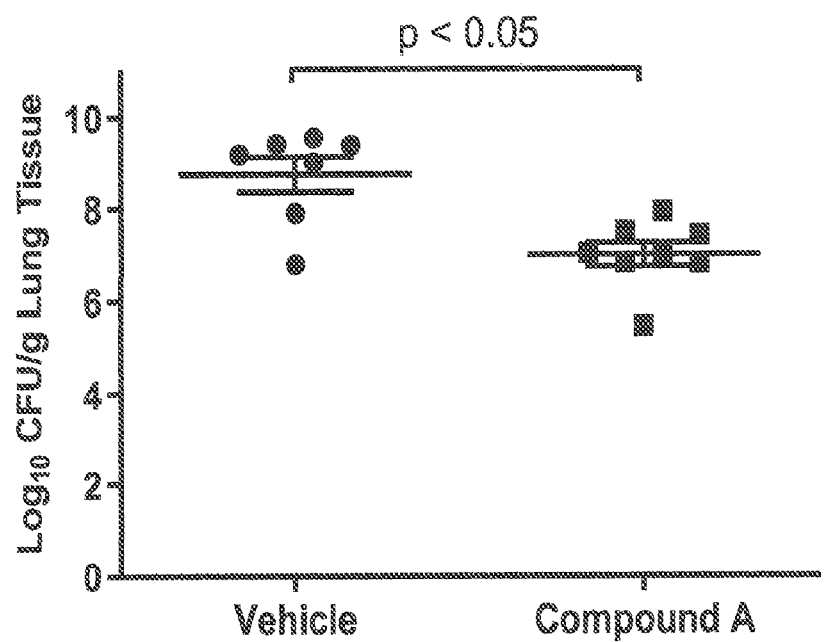

In this study, Composition A lot 5-266-01 was intratracheally dosed at 3 concentrations, 19 mg/kg, 6 mg/kg and 2 mg/kg in 4 independent tests (022, 023, 024, and 026). Overall, vehicle, 19 mg/kg and 2 mg/kg were dosed to a total of 40 mice and 6 mg/kg were dosed to a total of 30 mice. The pooled survival data were plotted as shown in FIG. 9. At the 96-hour timepoint after bacterial challenge/nanosponge treatment, the survival rate in the vehicle-treated group was 26%. The survival rate was increased to 68%, 66% and 38% at the dose of 19 mg/kg, 6 mg/kg and 2 mg/kg, respectively. A significant improvement of the survival rate was observed with all 3 doses.

Inhibition of Pulmonary Bacterial Load

Figure 7:
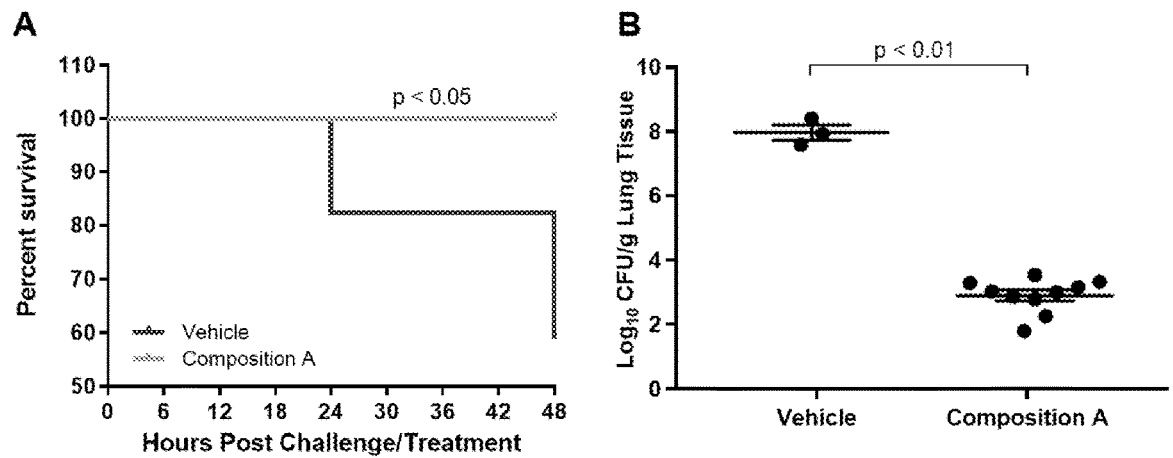

In the initial study (007), we demonstrated that Composition A lot 5-257-06 significantly reduced bacterial load in the lungs 48 hours after MRSA infection (FIG. 7). In this study (012), we examined if the inhibitory effect on bacterial load in the lungs was reproducible with a different lot of Composition A, 5-257-16. 5-257-16 was intratracheally dosed at 22.5 mg/kg immediately after bacterial instillation and the lungs of the mice were harvest 24 hours post challenge/treatment. The lung homogenate was plated for CFU count as described in the Method section. As shown in FIG. 10, 5-257-16 significantly reduced the bacterial load in the lungs of mice with MRSA pneumonia.

Example 4

Lung Exposure Assessment of Composition A Labeled with Fluorescent Tracer in Naïve Mice Summary A fluorescent version of Composition A, DiR-Composition A, was used to study the uptake, distribution and retention of DiR-Composition A in the lungs of mice after intratracheal administration. At the designated timepoints after administration of DiR-Composition A, mice were sacrificed and lungs were collected for ex vivo measurement of the fluorescence intensity of DiR-Composition A using a fluorescence imaging device or a fluorescence microplate reader. DiR-Composition A was taken up and distributed in the lungs rapidly after intratracheal administration; within 5 minutes it spread to the central and peripheral lung tissue with fairly uniformed distribution. DiR-Composition A retained in the lung for extended time; the estimated retention half-life of DiR-Composition A in the lung was 7-10 days.

Materials and Methods

Formulation and Characterization

Figure 15:
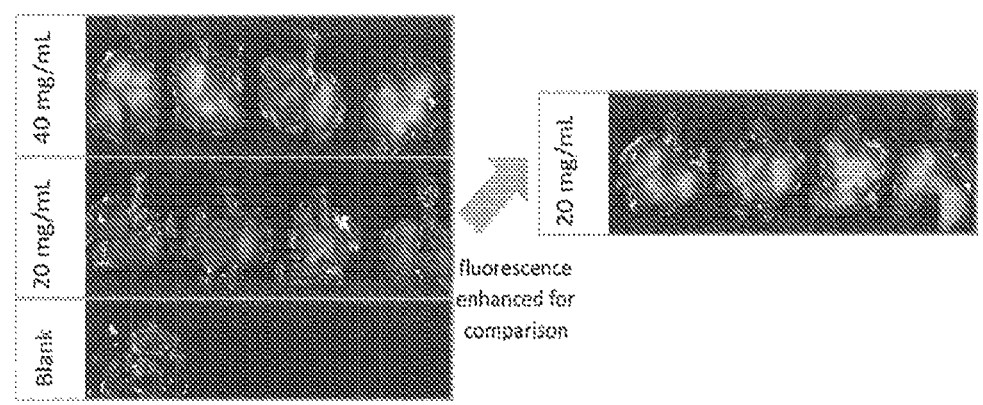
FIG. 15 illustrates exemplary uptake distribution of DiR-Composition A at two different concentrations. There is no or little difference between the uptake distribution of DiR-Composition A in the lungs of mice intratracheally administered with DiR-Composition A at 20 mg/mL (22 mg/kg) or 40 mg/mL (44 mg/kg).

To prepare fluorescently labeled Composition A, 0.1 weight percent of DiR dye dissolved in 10 μl of DMSO was added to the human RBC membrane prior to the addition of sphingomyelin and cholesterol. This solution was heated at 45° C. and stirred for one hour, then bath was sonicated for 10 minutes to incorporate all the DiR into the lipid bilayer of the RBC membrane. These dye molecules should insert directly into the lipid bilayer in a similar manner to sterols. After the RBC membrane labeling, cholesterol and sphingomyelin were added in the same way Composition A lots used in various efficacy studies were prepared. DiR-Composition A used in FIGS. 11-14 was fabricated using the same protocol as Composition A (lot 5-257-16). In FIG. 15, the protocol for batch 5-265-01 was used.

DiR-Composition A were characterized using dynamic light scattering (Malvern Analytical) to assess the size, polydispersity and zeta potential, and confirm similarity to the non-DiR labeled formulation. A dye stability test was carried out to evaluate the fluorescent stability of DiR-Composition A. For the release study, 20 kDa dialysis cups were placed in a large volume (1 L) PBS and 200 µl of 15 mg/mL DiR-Composition A was added inside each dialysis cup (n=3). Samples were capped and stirred slowly at 300 rpm for over a week. Ten (10) µl samples were taken at designated timepoints, and diluted 10× in water. Fluorescence intensity of samples was measured and compared to initial timepoints as well as internal controls to assess the stability of samples.

Animals and Husbandry

Female CD1 mice, 8 weeks old and between 25 and 30 g were ordered from Charles River Laboratories, and were acclimated to housing conditions and handled in accordance with Animal Use Protocol number S00227m, and in accordance with IACUC procedures. Mice were group-housed (5/cage) in disposable plastic cages on stainless steel racks, and were fed Teklad Global 2918 Rodent Diet and water ad libitum. Bedding were provided in the form of irradiated Teklad ⅛" corn cob bedding 7902. The environment was controlled to a temperature range of 74°±5° F. and a humidity range of 30-70%. Fluorescent lighting provided illumination for 12 hours per day.

Mice were acclimated for a minimum of 24 hours prior to study start. The animals were observed for general health and acceptability for use in this study. Only animals deemed healthy were included in this study.

Nanosponge Administration

Mice were anesthetized with ketamine and xylazine (90 mg/kg and 10 mg/kg intra peritoneally, respectively), and anesthetized mice were then held to an Otoscope tip, and the glottis and vocal cords visualized using the Otoscope magnifying glass and light source. A 30 µl volume of DiR-Composition A was pipetted into the trachea via gel-loading long plastic pipette tips. Mice were allowed to recover from anesthesia and return to the home cages. N=3/test group was used in the studies.

Mice were closely observed throughout the study period for any signs of morbidity or health conditions. Mice were humanely euthanized at previously determined timepoints for the study via $CO_2$ overexposure, and secondarily, cervical dislocation. Lungs were dissected and stored in 2 mL screw top plastic tubes wrapped with aluminum foil.

In Vivo Imaging

Lungs dissected from mice were aligned according to group on a matte black background. IVIS fluorescent imaging device and software were used to photograph the lungs and overlay their corresponding fluorescence counts with the lung brightfield images taken simultaneously.

Lung Homogenization and Fluorescence Quantification

In some studies, lung tissues were homogenized in water with Quartz beads (between 10-20 beads) were added to each tube using a Bead Beater homogenizer for 60 seconds. Samples were plated in a 96 well plate, and fluorescence was measured using a plate reader at excitation 760 nm emission 805 nm. A background signal from a lung not dosed with DiR-Composition A was subtracted from the final results.

Results

DiR-Composition A Characterization

Figure 11:
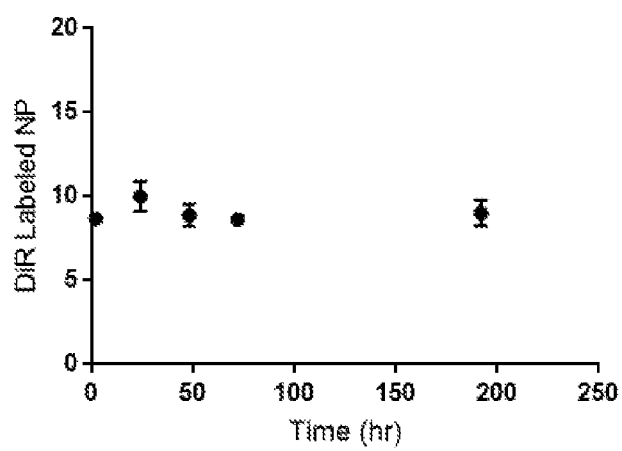

FIG. 11 shows the analysis of the size and stability of DiR-Composition A. The Table 3 below shows dynamic light scattering data of DiR-Composition A. The average size of DiR-Composition A was 98.6 nm, with a polydispersity index of 0.2 and D(50) of 67.2. These size and zeta potential measurements indicate a very similar formulation to the non-labeled Composition A. Size data is average of 3 independent measurements. The stability data shows the fluorescence intensity remains effectively the same after dialysis for over a week, suggesting the dye does not leak out of the lipid layers and remains embedded in the particles throughout the study.

TABLE 3

Dynamic light scattering data of DiR-Composition A

| Zeta Potential | Z-Ave | PDI | D(5) | D(50) | D(95) | D(10) |
|---|---|---|---|---|---|---|
| −2 mV | 98.57 | 0.206 | 35.9 | 67.2 | 182 | 40.8 |

Lung Uptake and Distribution of DiR-Composition A

Figure 12:
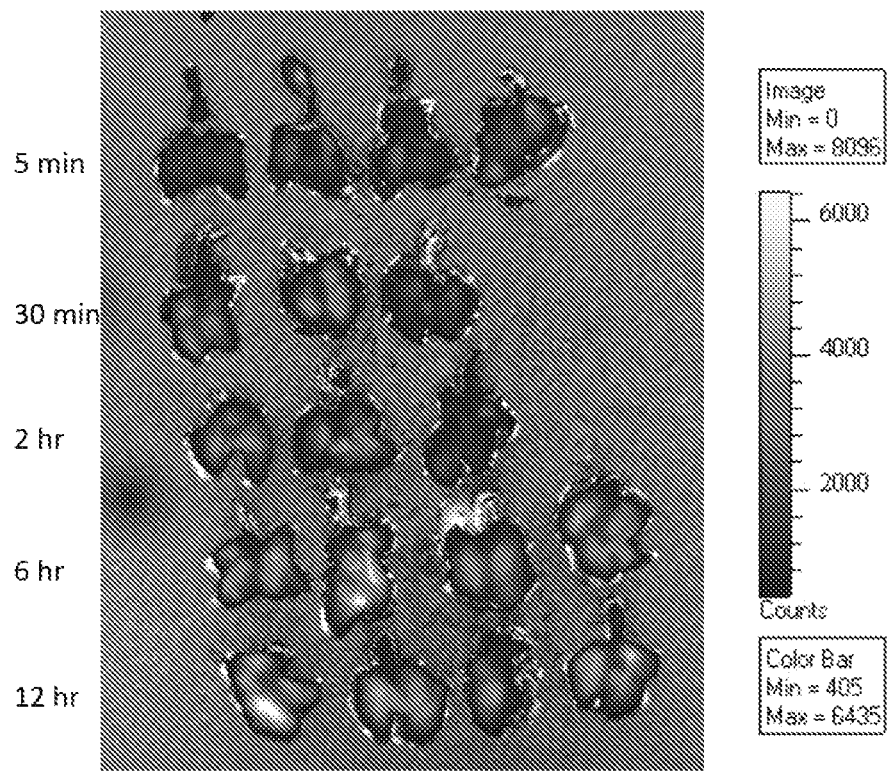

FIG. 12 shows the uptake and distribution of DiR-Composition A over the course of twelve hours after intratracheal administration. At the specified timepoints after intratracheal administration, mice were sacrificed and lungs were collected. The lung samples were imaged on an IVIS In Vivo Imager using the infrared fluorescence filter. At 5 minute post administration, DiR-Composition A distributed across the lung tissues at each timepoint with fairly even distribution and notable nanoparticle accumulation in most parts of the lungs. These results show that the nanosponges have good perfusion throughout the lungs even within 5 minutes. This indicates that there is little delay for the formulation to reach the peripherals of the lungs.

Pulmonary Retention of DiR-Composition a after Intratracheal Administration

Figure 13:
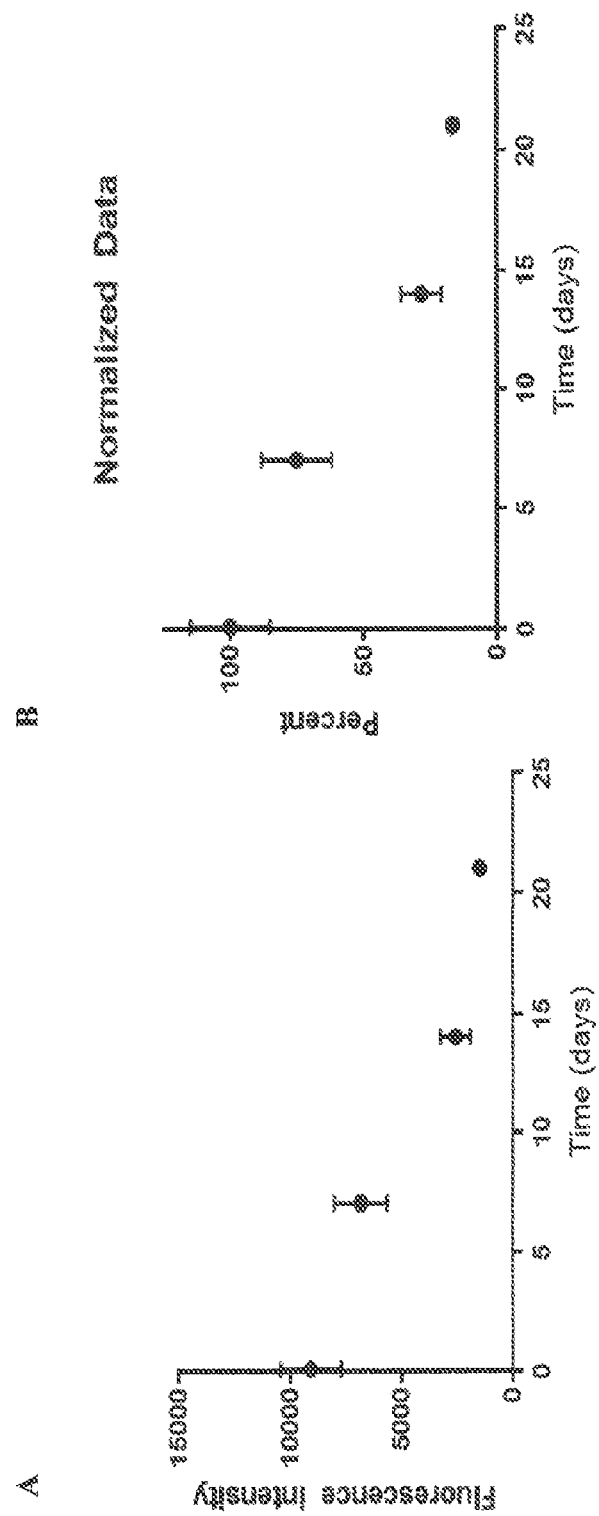
FIG. 13 illustrates exemplary retention time course of DiR-Composition A in the lungs of mice after intratracheal administration.
Figure 14:
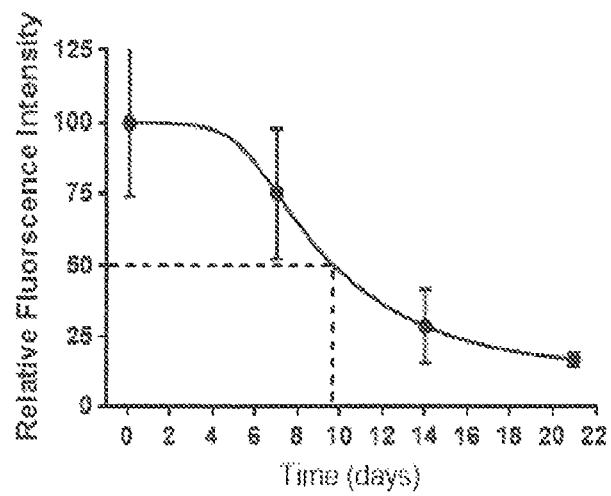
FIG. 14 illustrates exemplary retention time course of DiR-Composition A in the lungs of mice after intratracheal administration.

For the retention study shown in FIG. 13, mice (n=3) were intratracheally dosed with DiR-Composition A. At predetermined timepoints of 2 hours, 7 days, 14 days, and 21 days, 3 mice from each group were sacrificed. Lungs were resected and homogenized in 900 µl of water, then fluorescence was read via a plate reader (Excitation 760/Emission 805). Quantification of the lung fluorescence shows there is a decay of DiR-Composition A in the lungs over 3 weeks, with an estimated half-life of 7-10 days. The error bar between mice is plotted as standard error measurement (SEM). Signal was normalized to put 100% at the two-hour timepoint, and 0 was set as the background fluorescence of the lung tissue itself.

Effects of Highly Concentrated DiR-Composition A on Lung Delivery

In the studies in shown in FIGS. 11-14, nanosponge remained at 15 mg/mL, comparable to the 5-257-16 batch. To test the effect of nanosponge concentration on lung distribution, we created a highly concentrated batch of 46 mg/mL, reflecting the same method and concentration of batch 5-265-01. This batch was then diluted to 23 mg/mL to create a control similar to the prior studies. Mice were administered either 30 µl of 46 mg/mL or 23 mg/mL nanosponge. Mice were sacrificed 5 minutes after dosing, and lungs were imaged using the IVIS system.

FIG. 15 shows the distribution of nanoparticles in each group. In order to fairly assess spread of the nanosponges within the lungs, the 20 mg/mL group was also imaged at a longer fluorescence exposure in order to compensate for only having half the number of fluorophores in the same volume. Comparison between these groups shows that the higher concentrated particles distribute just as evenly and quickly as the lower concentration nanosponge, and no distinct differences were observed between each group.

CERTAIN REFERENCES

Berube B, Wardenburg J B, *Staphylococcus aureus* α-toxin: nearly a century of intrigue. Toxins. 2013, 5:1140-1166.
Bhakdi S, Tranum-Jensen J, Sziegoleit A, Mechanisn of membrane damage by streptolysin-O. Infection and Immunity. 1985 January 47(1):52-60.
Burhoe S. Blood groups of the rat (*Rattus norvegicus*) and their inheritance. Proceedings of the National Academy of Sciences. 1947, 32:102-109.
Choi K, Chang J, Lee M, Wang S, In K, Galano-tan J, Jun S, Cho K, Hwang Y, Kim S, Park W. Reference values of hematology, biochemistry, and blood type in cynomolgus monkeys from Cambodia origin. Lab Animal Research. 2016, 32(1): 46-55.
FDA Guidance for Industry: Estimating the Maximum Safe Starting Dose in Initial Clinical Trials for Therapeutics in Adult Healthy Volunteers, 2005. Available at https://www.fda.gov/downloads/Drugs/GuidanceCompliance-RegulatoryInformation/Guidances/UCM078932.pdf. Accessed Apr. 19, 2017.
FDA Guidance for Industry: Preclinical Assessment of Investigational Cellular and Gene Therapy Products, 2013. Available at https://www.fda.gov/biologicsblood-vaccines/guidancecomplianceregulatoryinformation/guidanc es/cellularandgenetherapy/ucm376136.htm. Accessed Apr. 19, 2017.
ICHS6(R1) Preclinical Safety Evaluation of Biotechnology-Derived Pharmaceuticals, 2011. Available at http://www-w.ich.org/fileadmin/Public_Web_Site/ICH_Products/Guidelines/Safety/S6_R1/Step4/S 6_R1_Guideline.pdf. Accessed Apr. 19, 2017.
Inoshima I., Inoshima N., Wilke G., Powers M., Frank K., Wang Y., Wardenburg J. B., A *Staphylococcus aureus* pore-forming toxin subverts the activity of ADAM10 to cause lethal infection in mice, Nat Med., 2012, 17, 1310-1314
Powers M. E., Kim H. K., Wang Y., Wardenburg J. B., ADAM10 mediates vascular injury induced by *Staphylococcus aureus* α-hemolysin, JID, 2012, 2016, 352-356
Schwartz L., Diafiltration for Desalting or Buffer Exchange, BioProcess International, 2003, 43-49
Wilke G. A., Wardenburg J. B., Role of a disintegrin and metalloprotease 10 in *Staphylococcus aureus* α-hemolysin-mediated cellular injury, PNAS, 2010, 107, 13473-78

What is claimed is:

1. A nanoparticle comprising an interior compartment and an outer surface comprising a cellular membrane isolated from a cell, said interior compartment not providing a solid support to said cellular membrane in said outer surface, and wherein:
    a) said interior compartment comprises a liquid that is isotonic to a human cellular or physiological liquid; and
    b) said outer surface comprises a steroid at a level from 40% (w/w) to 45% (w/w) and a sphingolipid at a level from 40% (w/w) to 50% (w/w), and from 10% (w/w) to 20% (w/w) said cellular membrane isolated from said cell, and
    wherein said nanoparticle is prepared by an in vitro process.

2. The nanoparticle of claim 1, wherein the interior compartment comprises a liquid that is isotonic to a human cellular liquid.

3. The nanoparticle of claim 1, wherein the interior compartment comprises a liquid that is isotonic to a human physiological liquid.

4. The nanoparticle of claim 1, wherein the cellular membrane comprises a plasma membrane.

5. The nanoparticle of claim 1, wherein the steroid is a cholestane, a cholane, a pregnane, an androstane, or an estrane, or the steroid is selected from the group consisting of a gonane, testosterone, cholic acid, dexamethasone, lanosterol, progesterone, medrogestone, β-sitosterol, cholesterol, and 5α-cholestane.

6. The nanoparticle of claim 1, wherein the outer surface comprises 40% (w/w) of the steroid.

7. The nanoparticle of claim 1, wherein the outer surface comprises 45% (w/w) of the steroid.

8. The nanoparticle of claim 1, wherein the interior compartment has a pH ranging from about 4 to about 10.

9. The nanoparticle of claim 1, which further comprises a releasable cargo.

10. The nanoparticle of claim 1, wherein the nanoparticle lacks cytoplasmic constituents of the cell from which the cellular membrane is isolated.

11. The nanoparticle of claim 1, wherein the interior compartment comprises a salt, a sugar or a sugar alcohol.

12. The nanoparticle of claim 1, wherein the interior compartment comprises a sugar or a sugar alcohol, and the outer surface comprises a plasma membrane isolated from a red blood cell.

13. The nanoparticle of claim 1, wherein the outer surface comprises the sphingolipid at a level of 45% (w/w).

14. The nanoparticle of claim 1, wherein the steroid is cholesterol.

15. The nanoparticle of claim 1, wherein the sphingolipid is sphingomyelin.

16. An immunogenic composition, which comprises an effective amount of a nanoparticle of claim 1.

* * * * *